US011197615B2

(12) United States Patent
Broderick

(10) Patent No.: US 11,197,615 B2
(45) Date of Patent: Dec. 14, 2021

(54) NONINVASIVE ELECTROACTIVE PHOTONIC PROTEIN NANOSENSOR WITH POLYMER PHOTOVOLTAIC OPTICS FOR MEMORY TRANSDUCTION USING ORGANIC AND INORGANIC ELEMENTS AS PLATFORMS

(71) Applicant: RESEARCH FOUNDATION OF THE CITY UNIVERSITY OF NEW YORK, New York, NY (US)

(72) Inventor: Patricia A. Broderick, Bronx, NY (US)

(*) Notice: Subject to any disclaimer, the term of this patent is extended or adjusted under 35 U.S.C. 154(b) by 487 days.

(21) Appl. No.: 16/074,254

(22) PCT Filed: Dec. 28, 2016

(86) PCT No.: PCT/US2016/068879
§ 371 (c)(1),
(2) Date: Jul. 31, 2018

(87) PCT Pub. No.: WO2017/117223
PCT Pub. Date: Jul. 6, 2017

(65) Prior Publication Data
US 2019/0142276 A1    May 16, 2019

Related U.S. Application Data

(60) Provisional application No. 62/273,693, filed on Dec. 31, 2015.

(51) Int. Cl.
*A61B 5/1455* (2006.01)
*A61B 5/00* (2006.01)
(Continued)

(52) U.S. Cl.
CPC .......... *A61B 5/0093* (2013.01); *A61B 5/0075* (2013.01); *A61B 5/1455* (2013.01);
(Continued)

(58) Field of Classification Search
None
See application file for complete search history.

(56) References Cited

U.S. PATENT DOCUMENTS

2007/0026440 A1    2/2007    Broderick et al.
2007/0158642 A1    7/2007    Gruner
(Continued)

FOREIGN PATENT DOCUMENTS

WO    WO2015021143    2/2015

OTHER PUBLICATIONS

Written Opinion of the International Searching Authority for PCT Application No. PCT/US2016/068879, dated Mar. 8, 2017, pp. 1-6.

*Primary Examiner* — Eric F Winakur
*Assistant Examiner* — Marjan Fardanesh
(74) *Attorney, Agent, or Firm* — Hoffmann & Baron, LLP

(57) ABSTRACT

An electroactive photonic polymer sensing device includes an imaging component that uses photonic energy to generate a photocurrent that represents a molecular parameter, wherein the imaging component includes a photosensitive material and at least one of a laser diode and/or photodiode; and a memory component that stores a representation of the molecular parameter, wherein the memory component includes at least one of a protein, vitamin, lipid, carbon allotrope, carbon tetra fluoride. A method of sensing polymers using an electroactive photonic sensing device includes converting, using an imaging component, photonic energy into electrochemical energy to generate a photocurrent that represents a molecular parameter, wherein the imaging device includes a photosensitive material and at least one of a laser diode and/or photodiode; and storing, using a memory component, a representation of the molecular
(Continued)

parameter, wherein the memory component includes at least one of a vitamin, lipid, carbon allotrope, carbon tetra fluoride.

25 Claims, 14 Drawing Sheets

(51) Int. Cl.
    *A61B 5/1477*     (2006.01)
    *A61N 5/06*     (2006.01)
    *G01N 33/66*     (2006.01)
    *A61B 5/145*     (2006.01)
    *A61B 5/1473*     (2006.01)
    *A61B 5/1459*     (2006.01)

(52) U.S. Cl.
    CPC ........ *A61B 5/1477* (2013.01); *A61B 5/14546* (2013.01); *A61B 5/4064* (2013.01); *A61B 5/4094* (2013.01); *A61N 5/06* (2013.01); *A61N 5/062* (2013.01); *A61N 5/0622* (2013.01); *G01N 33/66* (2013.01); *A61B 5/0051* (2013.01); *A61B 5/1459* (2013.01); *A61B 5/1473* (2013.01); *A61B 2560/0475* (2013.01); *A61B 2562/0285* (2013.01)

(56) References Cited

U.S. PATENT DOCUMENTS

| | | |
|---|---|---|
| 2008/0315091 A1 | 12/2008 | Morris et al. |
| 2014/0243934 A1 | 8/2014 | Vo-Dinh et al. |
| 2014/0358199 A1 | 12/2014 | Lim |

NONINVASIVE ELECTROACTIVE PHOTONIC PROTEIN NANOSENSOR WITH POLYMER PHOTOVOLTAIC OPTICS FOR MEMORY TRANSDUCTION USING ORGANIC AND INORGANIC ELEMENTS AS PLATFORMS

CROSS-REFERENCE TO RELATED APPLICATIONS

This application is a U.S. National Phase application of International Application No. PCT/US16/68879, filed Dec. 28, 2016, which claims the benefit of U.S. Provisional Application No. 62/273,693, filed Dec. 31, 2015, the disclosures of which are incorporated by reference herein in their entireties.

BACKGROUND

Field

The disclosed embodiments relate to a photosensitive, electroactive, polymer sensing device or nanosensor that operates by converting photonic energy into electrochemical energy to image neurochemicals in real time, which is non-invasive and/or minimally invasive, and used for neurodegenerative and psychiatric disorders in humans and animals including, but not limited to, diseases of the motor and sensory systems, such as the eye, brain, and skin.

Related Art

Voltammetric measurements can be used to detect certain biogenic substances in the brain of rats (Kissinger, P. T.; Hart, J. B.; Adams, R. N.; "Voltammetry in Brain Tissue—A New Neurophysiological Measurement", Brain Research, 55 (1973), p. 209). Other researchers have detected signals in the brains of living rats (McCreery, et al., Brain Res. Vol. 73 (1974), p. 23; Gonon, et al., Brain Res. Vol. 223 (1981), p. 69; Lane, et al., J. Electroanal. Chem., Vol. 95(1979), p. 117; Clemens and Phebus, Brain Res., Vol 267(1983), p. 183 and Millar, et al., Eur. J. Pharmacol. Vol. 109(1985), p. 341).

There has been little or no description of circuitry for in vivo electrochemical circuits. However, certain improvements have been made for in vitro voltammetric measurements since the linear scan for in vivo electrochemistry method was described for measuring biogenic chemicals. One such improvement was the in vitro processing of a linear scan current signal as the first half-derivative of the linear signal (Oldham, "Analytical Chemistry" Vol. 45 (1973) p. 39 and U.S. Pat. No. 3,868,578; Kanazawa, U.S. Pat. No. 4,449,552). However, neither Oldham nor Kanazawa describes circuitry applicable for detecting organic materials in living organisms. Although they describe oxidation and reduction reaction species, they do not describe cathodic (reduction) currents in vivo. Cathodic current is defined as current based on the acquisition of electrons by neurochemicals within the organ or suborgan and flowing away from and/or on an indicator electrode situated within the organ or suborgan. Anodic current is defined as current based on the loss of electrons by neurochemicals in the organ or suborgan and flowing toward and/or on an indicator. When applied to the brain, or other body organs, this type of processing (the first half derivative of the linear signal) should result in a semidifferentiated voltammogram having sharper peaks, which then allows greater separation between peaks representing chemical substances and which are easier to read than linear voltammograms. Conventional methods do not allow sharply defined individual detection of amines due to similar electrochemical potentials for biogenic amines set by the catechol moiety of the amines. Chronoamperometry, for example, does not allow direct, individual, and simultaneous detection of the biogenic amines. Semiderivation or semidifferentiation of the signal briefly allowed somewhat better detection. Many practitioners, however, have found it difficult or impossible to obtain routinely reproducible measurements using what is known as the in vivo electrochemistry technique of semiderivative or semidifferential voltammetry.

Although telemetric devices have been produced, as described in U.S. Pat. No. 4,424,812 (Lesnick) and U.S. Pat. No. 3,882,277 (DePedro), telemetric devices for monitoring brain signals have not been described. Neither of these patents describe monitoring signals produced electrochemically, either in vivo, in vitro, or in situ.

The prior art indicates that an oxidation current, or anodic current, should be used to detect biochemical species in the brain. Previous researchers assumed that in living systems, all chemical species that could be detected by electrochemical signals were converted into stable oxidized species. Most of the previous researchers also assumed that all biogenic chemical reactions produced oxidized species without producing stable reduced species. These assumptions have provided only a limited tool for diagnosing the mental and physiological states of living organisms, as only a limited number of biogenic chemicals can be detected using prior art methods. In U.S. Pat. No. 4,883,057, a cathodic current for measuring biogenic chemicals with a semiderivative circuit in vivo and in vitro is described.

Indicator microelectrodes pass small but measurable currents while neurotransmitters and metabolites close to the microelectrode surface undergo oxidation and/or reduction (Adams R N et al., 1982, Handbook of Psychopharmacology, pp. 1-74). When an electrode is placed in contact with a solution, a phase boundary is created that separates identical solutes into two different types. They are (a) molecules that are at a distance from the microelectrode, and (b) those molecules that are close enough to participate in mutual interactions between the surface of the microelectrode and the sample solution interface (Kissinger P T et al., 1996, Laboratory Techniques in Electroanalytical Chemistry, pp. 11-50). Collectively, these interactions are called electrochemistry.

Detection of electrochemical signals from solutions and from anatomic brain sites is termed "faradaic" because the amount of the oxidative and/or reductive species detected at the surface of the microelectrode may be calculated by a derivation of Faraday's Law, the Cottrell Equation, $$i^t = \frac{nFAC_0 D_0^{1/2}}{3.14^{1/2} t^{1/2}},$$

wherein i is current at time t, n is the number of electrons (eq/mol), F is Faraday's constant (96,486 C/eq), A is electrode area (cm$^2$), C is oxygen concentration (mol/cm$^3$), and D is the diffusion coefficient of oxygen (cm$^2$/s). The proportionality between charge and mass of an electrochemical reaction describes the relationship between the charge of each neurochemical in the process of oxidation and/or reduction and the concentration of each neurochemical. The Cottrell Equation relates to quiet solution experiments, wherein the potential is instantaneously switched from an initial value $E_i$ to a final potential, then held constant for a fixed time, then switched back to $E_i$. If material diffuses to a planar electrode surface in only one direction (linear diffusion) then the exact description of the current-time curve is the Cottrell Equation.

Current-time relationships with a circular electrode are defined in electrochemistry by the Cottrell Equation. Other electrode sizes and experiments using different electrolysis times were considered deviations from the Cottrell Equations that could be considered negligible. However, Wightman et al. observed that linear diffusion is not enough to describe the action that takes place at spherical microelectrodes (Dayton M A et al., 1980, Anal. Chem. 52:948-950). The quiet solution behavior of very small electrodes is different and is better described by a steady state equation in which the radius of the electrode is taken into account (Adams R N et al., 1982, Handbook of Psychopharmacology, pp. 1-74). This equation is suitable for calculating the edge effect or spherical steady-state contribution for even a 300-micron diameter electrode. Such a calculation reveals that the edge effect or spherical steady-state contribution adds approximately 30% current to the linear diffusion component for an electrolysis time of only one second (Dayton M A et al., 1980, Anal. Chem. 52:948-950).

Microvoltammetric circuits using several types of stearate-carbon paste microelectrodes were developed and refined (Broderick P A, 1995, U.S. Pat. No. 5,433,710; Broderick P A, 1996, EP 90914306.7; Broderick P A, 1999, U.S. Pat. No. 5,938,903, which are incorporated herein by reference). Reliable separation and quantification of neurotransmitters including norepinephrine, serotonin, and dopamine, as well as some of their precursors and metabolites is now possible (Broderick P A, 1989, Brain Res. 495:115-121; Broderick P A, 1988, Neurosci. Lett. 95:275-280; Broderick P A, 1990, Electroanalysis 2:241-245).

One electrode for in vivo electrochemical studies was developed in the laboratory of Ralph Adams (Kissinger P T et al., 1973, Brain Res 55:209). Using carbon paste electrodes with diameters reaching 1.6 mm and Ag/AgCl (3M NaCl) reference electrodes, neurotransmitters including dopamine and norepinephrine and their metabolites were detected (not separated), as a single peak in rat caudate nucleus with finite current electrochemistry and cyclic voltammetry.

Extensive refinements to microelectrodes and to in vivo electrochemistry have been made (Broderick P A, 1990, Electroanalysis 2:241-245). The development of a stearate-carbon paste probe along with an electrode conditioning process has resulted in reliable separation and detection of norepinephrine, dopamine, and serotonin (Broderick P A, 1996, EP 90914306.7; Broderick P A, 1999, U.S. Pat. No. 5,938,903). In addition, other types of microelectrodes with increased sensitivity and reliability were developed (Broderick P A, 1996, EP 90914306.7; Broderick P A, 1999, U.S. Pat. No. 5,938,903). An electrochemically pre-treated carbon fiber electrode allows the differentiation of dopamine from DOPAC (Akiyama R A et al., 1985, Anal Chem. 57:1518), as do microelectrodes.

Previous in vitro analysis techniques have yielded disappointing results. Prior ex vivo studies attempted to circumvent these problems with a microdialysis technique (During M J et al., 1993, Lancet 341:1607-1610; Lehmann A et al., 1991, Neurotransmitters and Epilepsy, pp. 167-180). Dialysis tubing placed on or within the brain is perfused with artificial CSF or Krebs-Ringer bicarbonate solution, and the perfusate is then analyzed with High Performance Liquid Chromatography (HPLC) with electrochemical detection, which provides information about the extracellular environment. However, this technique has been criticized because of the local gliosis caused by the dialysis probes and the perfusion process that can alter the biochemical parameters under study. In addition, the perfusate is analyzed outside the brain and, therefore, in contrast to microvoltammetry measurements are not truly in situ or in vivo.

Epilepsy is a neurological disorder characterized by transient electrical disturbances of the brain that may be studied by electrophysiological techniques. Neurotransmitter data from experimental epilepsy models and in vitro analysis of surgically resected specimens from patients with partial epilepsy have yielded conflicting results. These conflicting results may be due to significant variations between samples, as well as choice of controls. Additionally, highly localized changes in epileptic cortex are not detectable using whole tissue homogenates. In general, increased activity in noradrenergic, dopaminergic, and serotonergic systems are believed to reduce cortical excitability and decrease seizure activity (Delgado-Escueta A V, 1984, Ann Neurol. 16(Suppl.): 145-148). However, human temporal lobe epilepsy is a complex disorder that may involve the dysfunction of distinct neuronal systems including the hippocampus and entorhinal cortex, the temporal neocortex, or combinations of these structures. Therefore, the contribution of different neurotransmitter systems to epileptogenesis in a given patient likely varies with lesion location and the etiology of epilepsy. Furthermore, studies demonstrating presynaptic inhibitory serotonin autoreceptors in the hippocampus (Schlicker E et al., 1996, Naunyn Schmiedebergs Arch Pharmacol. 354:393-396) and a dual role for norepinephrine in epileptogenesis (Radisavljevic Z et al., 1994, International Journal of Developmental Neuroscience 12:353-361) suggest an even more complex situation.

Studies are defining a syndrome of neocortical temporal lobe epilepsy that has distinct clinicopathologic and electrophysiologic features from mesial temporal lobe epilepsy (Pacia S V et al., 1997, Epilepsia 38:642-654; Pacia S V et al., 1996, Ann Neurol 40:724-730). While both mesial temporal lobe epilepsy and neocortical temporal lobe epilepsy are potentially treatable with surgical resection when seizures are refractory to antiepileptic medication, the type and extent of temporal lobe resection necessary to achieve a seizure free outcome may differ. Neocortical temporal lobe epilepsy patients may require resections tailored to include the epileptogenic zone. These resections may lie outside the boundaries of a standard temporal lobe resection performed for mesial temporal lobe epilepsy. Neurochemistry using microvoltammetry provides a means for defining the epileptogenic zone in these patients.

Other techniques for detecting neurotransmitters in real time and in vivo fall short. These methods, such as dialysis, have limitations such as those described in During M J et al., 1993, Lancet 341:1607-1610; Ferrendelli J A et al., 1986, Adv. Neurol. 44:393-400; Goldstein D S et al., 1988, J Neurochem 50:225229; Janusz W et al., 1989, Neurosci Res 7:144153; Kawaguchi Y et al., 1998, J Neurosci 18:6963-6976.

In vivo detection of neurotransmitters and other chemicals is also important for diagnosing and treating movement disorders, such as spinal cord injuries and brain injuries. These techniques are limited, in part, by their relative inability to monitor neural chemistry in real time in a freely behaving animal or human, which may limit their diagnostic and/or therapeutic efficacy. Movement may be generated by a central pattern generator (CPG) i.e., a neuronal network capable of generating a rhythmic pattern of motor activity either in the presence or absence of phasic sensory input from peripheral receptors.

Central pattern generators (CPG) have been identified and analyzed in rhythmic motor systems and CPGs can generate a variety of motor patterns. A universal characteristic of this wide variety of motor patterns is that they consist of rhythmic and alternating motions of the body or appendages. It is this rhythmicity that make these behaviors appear stereotypic. It is the repetitive quality of these behaviors that enables stereotypic behaviors to be controlled automatically. This automaticity or autoactivity means that there may be little or no need for intervention from higher brain centers when the environment remains stable.

The simplest CPGs contain neurons that are able to burst spontaneously. Such endogenous bursters can drive other motor neurons, and some motor neurons are themselves, endogenous bursters. Importantly, bursters are common in CPGs that produce continuous rhythmic movement, such as locomotion. However, locomotion is an episodic, rhythmic behavior, and thus further regulation by neurochemicals becomes necessary. Endogenous bursts (cell firing) of neurons involved in locomotion are regulated by neurotransmitters and neuromodulators, i.e., substances that can alter the cellular properties of neurons involved in CPGs. Brief depolarizations occur and lead to maintained depolarizations (plateau potentials) that can last for long periods of time. These maintained depolarizations far outlast the initial depolarization, and it is these maintained depolarizations that are necessary for rhythmic movements. The generation of rhythmic motor activity by CPGs can be altered by amines and peptides (Grillner S et al., 1987, Trends Neurosci. 10:34-41; Rossignol S et al., 1994, Curr. Opin. Neurobiol. 4:894-902), thereby enabling a CPG to generate an even greater variety of repetitive motor patterns. Motor CPGs produce a complex temporal pattern of activation of different groups of motor functions and each pattern can be divided into a number of distinct phases even within a phase. CPGs are time-dependent (Pearson K et al., 2000, Principles of Neural Science, 4th edition, pp. 738-755).

Serotonin is an important neuromodulator for CPGs and can control the CPG underlying the escape swim response in the mollusc, Tritonia diomedea. The dorsal swim interneurons (DSIs) are a bilaterally represented set of three 5-HTergic neurons that participate in the generation of the rhythmic swim motor program. Serotonin from these CPG neurons functions as both a fast neurotransmitter and as a slower neuromodulator. In its modulatory role, 5-HT enhances the release of neurotransmitter from another CPG neuron, C2 and also increases C2 excitability by decreasing spike frequency adaptation. Serotonin intrinsic to the CPG may neuromodulate behavioral sensitization and habituation. Serotonin intrinsic to the DSI enhances synaptic potentials evoked by another neuron in the same circuit (Katz P S, 1998, Ann. NY Acad. Sci. 860:181-188; Katz P S et al., 1994, Nature 367:729-731).

In another mollusc, the pteropod, Clione limacina, the CPG for swimming is located in the pedal ganglia and formed by three groups of interneurons which are critical for rhythmic activity. The endogenous rhythmic activity of this CPG is enhanced by 5-HT (Arshaysky Y I et al., 1998, Ann NY Acad. Sci. 860:51-69). In the pond snail, Lymnaea stagnalis, 5-HT is the main neurotransmitter in its stereotypic feeding circuit (Sadamoto H et al., 1998, Lymnaea Stagnalis. Neurosi. Res. 32:57-63). In the sea slug, Aplysia, the CPG for biting is modulated both intrinsically and extrinsically. Intrinsic modulation has been reported to be mediated by cerebral peptide-2 (cp-2) containing CB1-2 interneurons and is mimicked by application of CP-2, whereas extrinsic modulation is mediated by the 5-HT-ergic metacerebral cell (MCC) neurons and is mimicked by application of 5-HT (Morgan P T et al., 2000, J. Neurophysiol. 84:1186-1193).

In vertebrates, the 5-HT somatodendritic nuclei, the raphe, comprise the most expansive and complex anatomic and neurochemical system in CNS. Raphe nuclei almost exclusively reside along the midline in the rat and in the primate. Fewer reside along the midline, but several exhibit a paramedian organization (Azmitia E C, 1986, Adv. Neurol. 43:493-507). The rostral 5-HT raphe group and caudal linear nucleus sends 5-HT efferents to A9 basal nuclei motor systems and the caudal 5-HT group, whereas the interfascicular aspect of the 5-HTergic dorsal raphe projects efferents to A10 basal ganglia (nuclei) regions (Jacobs B L et al., 1992, Physiol. Rev. 72:165-229).

Electrophysiological studies have shown that the most prominent action of increased 5-HT cell firing, in 5-HT somatodendrites in treadmill locomotion for example, is to increase the flexor and extensor burst amplitude of 5-HT cell firing in dorsal raphe, (DR) somatodendrites for 5-HT, during locomotion (Barbeau H et al., 1991, Brain Res. 546:250-260). Further evidence for 5-HT controlling motor output is seen from studies in which 5-HT, directly injected into the motor nucleus of the trigeminal nerve, increased the amplitude of both the tonic electromyogram of the masseter muscle and the externally elicited jaw-closure (masseteric) reflex (McCall R B et al., 1979, Brain Res. 169:11-27; McCall R B et al., 1980, Eur. J. Pharmacol. 65:175-183; Ribeiro-Do-Valle L E et al., 1989, Soc. Neurosci. Abstr. 15:1283). In fact, Jacobs and Azmitia have proposed that 5-HT's primary function in CNS neuronal circuitry is to facilitate motor output (Jacobs B L et al., 1992, Physiol. Rev. 72:165-229).

Serotonin neurons within 5-HT somatodendrites depolarize with such regularity that they exhibit automaticity, i.e., they can act by a CPG and produce plateau potentials. Thus, 5-HT neurons exhibit repetitive discharge characteristics. Increased 5-HT neuronal cell firing in somatodendritic raphe nuclei generally precedes the onset of movement or even increased muscle tone in arousal by several seconds and is maintained during sustained behavior (Jacobs B L, 1986, Neurochemical Analysis of the Conscious Brain: Voltammetry and Push-Pull Perfusion, Ann NY Acad. Sci., pp. 70-79). 5-HT cell firing in raphe nuclei is sometimes phase-locked to repetitive behavioral stereotypic responses. The regular firing of 5-HT somatodendrites in raphe nuclei is activated preferentially. This activation is associated with locomotion and chewing, stereotypic behaviors that are stimulated by CPG's (Jacobs B L et al., 1991, Pharmacol. Rev. 43:563-578). Serotonin intrinsic CPG's have been reported to be responsible for inducing rhythmic motor activity in the spinal cord of the turtle and the lamprey (Guertin P A et al., 1998, Neurosci. Lett. 245:5-8; Harris-Warrick R M et al., 1985, J. Exp. Biol. 116:27-46). The evidence in the lamprey suggests that 5-HT may have a role in the generation of a family of related undulatory movements, including, swimming, crawling, and burrowing, by a single CPG.

Current imaging technology is limited with respect to tumor visualization in neural tissue. For example, magnetic resonance imaging MRI is limited in its ability to detect tumor infiltration into white matter. This may hinder a physician's ability to render a diagnosis and/or prognosis. It further limits the ability to treat the patient by, for example, hindering a surgeon from defining tumor boundaries to remove the tumor. Alternatively, an inability to visualize cancerous cells or tissue in white matter may hinder a physician's ability to monitor the efficacy of a chemotherapy regimen. Accordingly, there is a need for an improved nanosensor to detect neurotransmitters and neurological disorders.

SUMMARY

The embodiments disclosed herein are directed to a non-invasive or minimally invasive protein sensing device or nanosensor or neuroprobe used to treat patients and animals with brain diseases. The nanosensor enables the inside of the brain to be monitored without opening the brain, as is conventionally required. In addition to neurological disorders and injuries, the disclosed embodiments may be used for brain cancer diagnosis and treatment.

These embodiments provide substantial advancements in personalized medicine and the treatment of Parkinson's disease, Alzheimer's disease, epilepsy, stroke, and other brain diseases that occur because the brain is in trauma by enabling imaging of neurotransmitters and genes associated with neurotransmitters. Photons of light carrying the protein rhodopsin through ligand gated channels in the skull and brain produce an electrochemical current based on the photonic light energy enabling the conversion of light energy to electrical energy and creating a photoelectrical current in units and subunits of voltage. This photoelectrochemical current is monitored using a potentiostat, spectrometer, and/or a spectroelectrochemical chemiluminescence device.

The disclosed embodiments relate to a miniature photosensitive, electroactive polymer sensing device or nanosensor that operates by converting photonic energy into electrical and electrochemical energy that generates a photocurrent in the brain without opening the brain. The output is provided in units of voltage. Laser diodes then enable the electrochemical waveform to be seen as an electrochemical image in color separated into specific spectral frequencies. Thus, the photocurrent provides an image of neurochemicals in real time, noninvasively and/or minimally invasively. The embodiments provide a photoelectrochemical conductance device for nanodiagnostics, nanotherapies, and nanotheranostics. These embodiments are directly applicable to specific neurodegenerative and psychiatric disorders in humans and animals including, but not limited to, diseases of the motor and sensory systems in the brain, body, and blood. The disclosed embodiments interact with organ systems, such as the eye, brain, and skin in vivo, in vitro, and in situ. The embodiments further relate to a memory transduction device enabled by polymeric molecular bonding using highly polar covalent hydrogen bonding intermolecularly. The embodiments include electrical devices that enable the discovery of novel target compounds to diagnose and treat disease by using anion-cation exchange properties with electrochemical reduction voltammetry control. The embodiments also relate to brain sensing using optoelectronics, and producing novel nanomedicines and optogenetics to identify unique and/or continuous patterns of neurotransmitters and neurotransmitter-related genes for spinal and brain repair.

The embodiments disclosed herein also utilize additional proteins that are luminescent. Human LIGHT is a type II membrane protein that is a member of the TNF superfamily (TNFSF14). LIGHT is an acronym for Lymphotoxins exhibit Inducible expression, and competes with HSV Glycoprotein D for HVEM, a receptor expressed by T-lymphocytes. LIGHT is also called HVEM-L and LT-gamma photosensitive serine protease inhibitors. The disclosed embodiments relate to inhibitors for serine proteases (thrombin, factor Xa, and chymotrypsin) that are light sensitive.

The embodiments disclosed herein also utilize a protein or proteins that can be made luminescent. Photosensitive material can be made by using hydrophobic bonds from phosphatidylcholine incorporated into the protein, and by using hydrophobic bonds of the photolysed complex with protease from *Staphylococcus aureus* and trypsin. The protein, albumin, can also be made photosensitive.

The embodiments disclosed herein further include a method of making proteins luminescent and making other materials that are not proteins luminescent.

The embodiments disclosed herein include chemiluminescent materials that are not photonic, but emit light during catalysis when a second compound is catalyzed from a first compound during the reassembly of electrons.

The embodiments disclosed herein include a nanosensor, which includes an imaging component that uses photonic energy to generate a photocurrent that represents a molecular parameter, wherein the imaging device includes a photosensitive material and at least one of a laser diode and/or photodiode; and a memory component that stores a representation of the molecular parameter, wherein the memory component includes at least one of a vitamin, lipid, carbon allotrope, and/or carbon tetra fluoride.

The photosensitive material may include at least one of a protein, glycoprotein, protease, peptide, amino acid, opsin, retinal, retinoic acid, retinol, rhodopsin, bathorhodopsin, lumirhodopsin, metarhodopsin 1, metarhodopsin 11, lumirhodopsin, trans-retinal, purple membrane proton pump protein microbe from a class of helobacteria, eukaryote, prokaryote, vitamin. The memory component may transduce a memory profile of a half wave of a molecule, and provide a peak signature associated with the molecule in an excited state proton transfer (ESPT). The electroactive photonic polymer sensing device may include a potentiostat monitoring photoelectrochemical current derived from the imaging component, and a spectrometer detecting and representing light energy derived from the imaging component. The laser diode may provide low wattage, such as but not limited to hundreds of watts or less, near infrared energy configured to extend approximately 30 mm into neuroanatomy of a brain, and the imaging component may include at least one of a conducting component, semiconducting component. The conducting component may include at least one of a silica-containing material, piezoelectric material, and the semiconducting component may include tetrafluoromethane. The imaging component may include rhodopsin, the memory device may include carbon fullerene, and the rhodopsin and carbon fullerene may be disposed in a polymer shell.

The embodiments disclosed herein also include a method of sensing polymers, which includes converting, using an imaging component, photonic energy into electrochemical energy to generate a photocurrent that represents a molecular parameter, wherein the imaging component includes at least one of a laser diode, photodiode, and/or photosensitive material; and storing, using a memory component, a representation of the molecular parameter, wherein the memory device includes at least one of a vitamin, lipid, carbon allotrope, and/or carbon tetra fluoride.

The photosensitive material may include at least one of a protein, glycoprotein, protease, peptide, amino acid, opsin, retinal, retinoic acid, retinol, rhodopsin, bathorhodopsin, lumirhodopsin, metarhodopsin 1, metarhodopsin 11, clumirhodopsin, trans-retinal, purple membrane proton pump protein microbe from a class of helobacteria, eukaryote, prokaryote, and/or vitamin. The method may include transducing a memory profile of a half wave of a molecule, and providing a peak signature associated with the molecule in an excited state proton transfer (ESPT). The method may include monitoring photoelectrochemical current derived from the imaging component using a potentiostat, and detecting and representing light energy derived from the imaging component using a spectrometer. The method may include configuring the laser diode to provide near infrared energy to extend approximately 30 mm into neuroanatomy of a brain, and configuring the imaging component to include at least one of a conducting component, semiconducting component. The method may include configuring the conducting component to comprise at least one of a silica-containing material, and/or piezoelectric material, configuring the semiconducting component to comprise tetrafluoromethane, configuring the imaging component to comprise rhodopsin; configuring the memory component to comprise carbon fullerene; and disposing the rhodopsin and carbon fullerene in a polymer shell.

The embodiments disclosed herein further include a computer-readable medium comprising instructions that, when executed by a processing device perform a method of sensing polymers, which includes converting, using an imaging component, photonic energy into electrochemical energy to generate a photocurrent that represents a molecular parameter, wherein the imaging component includes at least one of a laser diode, photodiode, and/or photosensitive material; and storing, using a memory component, a representation of the molecular parameter, wherein the memory device includes at least one of a vitamin, lipid, carbon allotrope, and/or carbon tetra fluoride.

Other embodiments will become apparent from the following detailed description considered in conjunction with the accompanying drawings. It is to be understood, however, that the drawings are designed as an illustration only and not as a definition of the limits of any of the embodiments.

BRIEF DESCRIPTION OF THE DRAWINGS

The following drawings are provided by way of example only and without limitation, wherein like reference numerals (when used) indicate corresponding elements throughout the several views, and wherein:

FIG. 5 shows a fiber optic cable assembly, in which the nanosensor shown in FIG. 3 is embedded or adjacent to;

FIG. 7B shows another embodiment of the optical protein nanosensor system;

Figure 1:
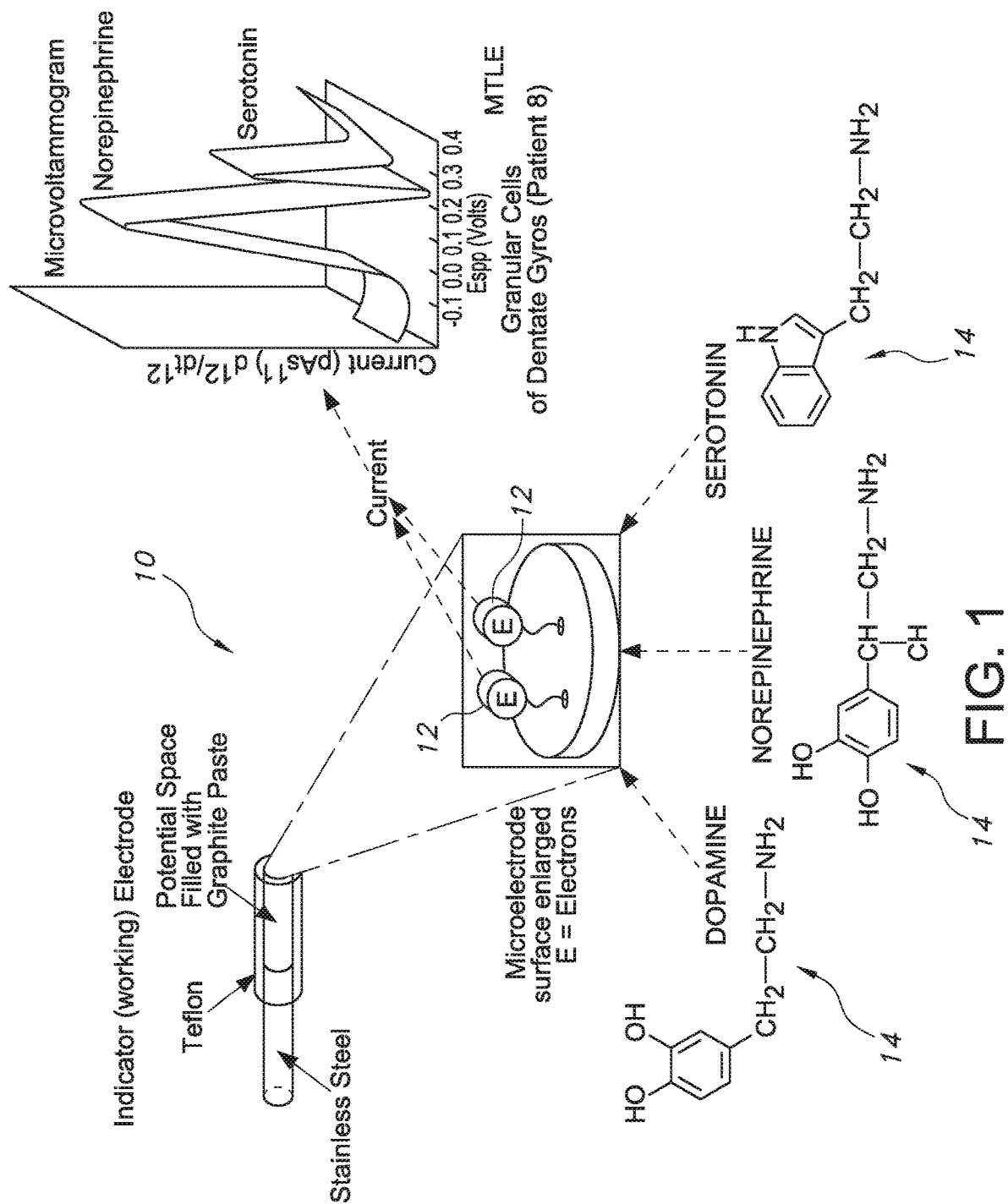
FIG. 1 shows the operation of a Broderick probe in detecting neurotransmitters and a microvoltammogram resulting therefrom.

It is to be appreciated that elements in the figures are illustrated for simplicity and clarity. Common but well-understood elements that are useful or necessary in a commercially feasible embodiment are not shown in order to facilitate a less hindered view of the illustrated embodiments.

DETAILED DESCRIPTION

A photonic electroactive nanosensor in accordance with embodiments disclosed herein includes organic elements, such as, proteins, lipoproteins, glycoproteins, proteases, peptides, amino acids, and/or photosensitive biomaterials, such as, opsin, retinal, retinoic acid, retinol and rhodopsin, bathorhodopsin, lumirhodopsin, metarhodopsin, metarhodopsin and trans-retinal (free). Examples of organic photosensitive elements include purple membrane proton pump protein microbes used by archeae, from the class of helobacteria, as well as eukaryotes and prokaryotes, and organic photosensitive carbon allotropes. The sensing device can also include vitamins, such as, α-tocopherol, and/or lipids.

In some embodiments, the sensing device can include organic conducting elements, such as, carbon and/or microbes. In some embodiments, the sensing device can include non-carbon conducting elements, such as silica containing materials, such as dioxosilane. In some embodiments, the sensing device can include inorganic semiconducting elements, such as tetrafluoromethane, and can further include organic and/or inorganic piezoelectric materials.

Photosensitive electro-active polymers of the disclosed embodiments enable molecular entities to be imaged through the skull and below the scalp without opening the skull. Without being bound by theory, is it believed that the polymer shell-based sensing device acts by using a series of intermolecular covalent, highly electronegative polar hydrogen bonds and London dispersion forces or bonds that polymerize with thermal catalysis. The sensing device tracks neurotransmitters, which are not limited to the conventional movement of electrons, but rather memorizes molecular entities while the subject moves, sleeps, and acts freely. The sensing device enables images to be generated of the natural, diseased, and surgically or medically treated states in real time of the same subject. The neurotransmitter that profiles the subject's outcome is seen by using a DC-to-AC converter or commutator coupled to a laptop, mobile phone, and/or computing device. The sensing device images anion-cation exchanges as electrically driven with a reduction circuit and incorporates elements of ultraviolet and ultrasound techniques using circuits, such as that shown in FIG. 15 of U.S. Pat. No. 5,938,903, which is incorporated by reference herein in its entirety.

A photoacoustic piezoelectric device acting on a temporal bone or tympanic membrane is activated to record the response of a photonic sound pulse in decibels. A miniaturized speaker is mounted above and behind the ear of the patient, which provides the background noise and/or stimuli. Responses are recorded at, for example 200 ms intervals, after presentation of the stimulus. The movement responses are transduced by a piezoelectric accelerometer. The patient's seizure movement from the decibel stimulus generates an electrical current in the piezoelectric nanosensor that distinguishes firing from non firing neurons. The nanosensor detects the pressure pushing down on the ear by photonic pulses on the piezoelectric ceramic platform due to the eliciting stimulus in decibels. Some of the disclosed embodiments are designed to minimize extraneous noise and vibrations to attenuate influences from external stimuli.

Photoacoustic responses to auditory stimuli via muscle movements transduced electrically use piezoelectric materials in epilepsy patients and patients with neurodegenerative diseases and/or psychiatric disorders and drug abuse. Data is recorded as a potential in voltage and concatenated for compatibility using, for example, spreadsheet software. The maximum voltage Vmax is used in calculations, which represents the highest voltage detected during the response window, which represents the peak value of the response.

The basic principle of acoustics measurement and piezo effect are as follows. The conversion of electrical pulses to mechanical vibrations and the conversion of the returned mechanical vibrations back into electrical energy is the basis for ultrasound testing. The transducer converts the electrical energy into acoustic energy. Piezo material is polarized material (i.e., some parts of the molecule are positively charged, while other parts of the molecule are negatively charged) with electrodes attached to two of opposing faces of the piezo material. When an electric field is applied across the material, the polarized molecules align themselves with the electric field, resulting in induced dipoles within the molecular or crystal structure of the material. In piezophotonics, semiconductors are important and relevant to the disclosed embodiments, as is photoacoustics in conjunction with piezo semiconductor properties.

The active element of acoustic transducers is typically ceramic, but can include other materials, such as cadmium and titanium. Piezoelectronics include semiconductors for imaging anions and cations in patients and animal brains. Pressure of the seizure ultrasound photonic energy changes from firing to non-firing sleep materials and alert system because the tympanic membrane is muscle and mechanical energy, which is provided by movement of the membrane with and without seizure.

Therefore, the disclosed embodiments can distinguish between epilepsy and non-epilepsy while also providing an alert system for the patient and animal during aura period, usually by the smell of burning rubber. Nanosensor photonics provide a substantially advantageous technique to study, diagnose, and avoid danger during seizure and aura. Disclosed embodiments include pattern profiling of a patient's need for personalized medicine, brain printing or an imprinting system for video-tracking neurotransmitters in real time and providing diagnosis, strategies for treatment, and solutions to underlying disorders previously unable to be reached or ascertained. Disclosed embodiments also provide a danger-free zone for epilepsy patients and animals.

Piezoactuators are electromechanical transducers that convert electrical signals into a mechanical displacement to regulate control systems and vice versa. The conversion process is the focus of actuator technology. Electric field strengths of about 2000 V/mm are used for an actuator deflection of 1.4 to 1.7, for example.

Figure 2:
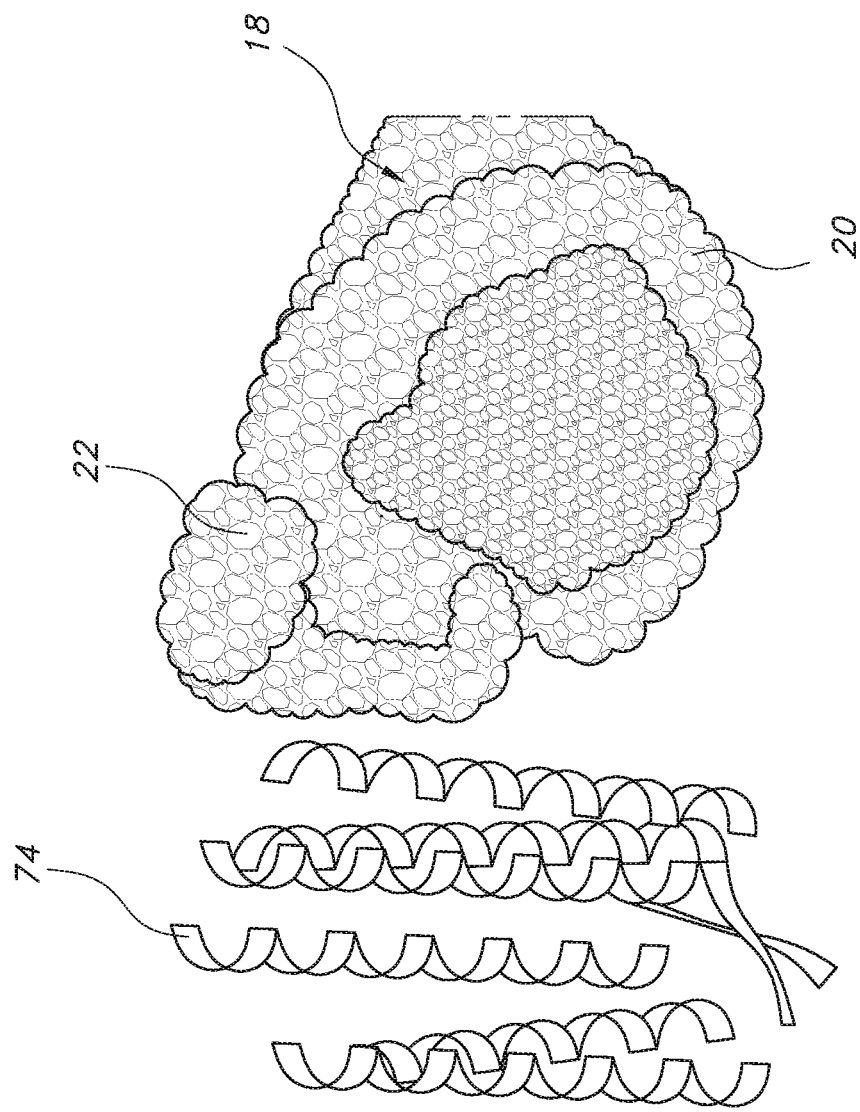
FIG. 2 shows a nanosensor in accordance with one or more of the disclosed embodiments.

In some embodiments, the sensing device includes a polymer shell 20 shown in FIG. 2. For example, the sensing device can include a carbon fullerene and an opsin 22 (e.g., rhodopsin) in the polymer shell 20. The polymer shell 20 can include several lipids and/or oils. The sensing device transduces a memory profile of the half wave of a molecule, which produces a peak signature for each target molecule in an excited state proton transfer (ESPT). The memory of the target molecule is embedded within the spaces of the sensing device and this template is trained to memorize anions and cations for diagnosis and treatment.

Memory in the polymer or protein rhodopsin nanosensor uses the photoelectric effect, which activates the photovoltaic effect by translating photonic potential energy to voltage. Rhodonine is a constituent of rhodopsin, is a known semiconductor, and may not be photosensitive, but photoreceptors in rhodopsin are used to detect photonic light. Near infrared may be safer than ultraviolet energy for humans and animals. Proteins can be made photosensitive, and photonic energy operates by semiconduction. Rhodopsin, when activated by near infrared or photonic light, acts as a semiconductor by excited state proton transfer (ESPT). The color change diagram in rhodopsin shows that when subtypes of rhodopsin convert, rhodopsin bleaches and changes color from its various states. For example, rhodopsin can change from being bleached to a green, to a red, and then to a black or inactive state. In this way, signaling occurs and memory sites, such as catecholamines and glutamates, for example, are detected in the brain, on-line, or in vivo within nanoseconds.

ESPT, which provides an improvement over conventional techniques, enables the embodiments of the nanosensor to operate by reassembling highly polar hydrogen bonds to substantially improve the imaging of targets in the brain to diagnose patients and animals. The brain includes sites for charges, and neurons are charged cells; much like an electronic device using anode/cathode circuits, neurons in the brain, body, and blood are electronic devices using anode/cathode circuits. The nanosensor and a neuron act as a lock and key to anion cation exchanges using semiconductor properties. Thus, light enables semiconductor properties of the rhodopsin rhodonine nanosensor to chemically and magnetically bond with the semiconductor properties of the neuron. Semiconductor properties are known to behave as intermediates between conductors and insulators by using anode/cathode circuits that have an extra layer between the anode and the cathode. This extra layer is at an np heterojunction. A protonated part is the p layer or positively charged layer, which is also referred to as the protonated layer, and is formed by the addition of hydrogen bonds and protons. When photonic energy is present, the protonated positive layer passes protons to the extra layer between the anode and the cathode making the extra layer, the layer where the holes and spaces were, positive. The anode is negative, the n layer, or nonprotonated layer, and the previous holes and spaces are positive and protonated.

Memorization of molecular entities and concentrations takes place by excited state proton transfer. A newly formed sp3 valence layer enables movement and reassembling of both halves of a hydrogen bonds, which is highly polar covalent, to recognize and signal to the anode cathode counterparts in the neuron. Each reassembly of bonds forms a memory of the molecule under study, and with continuing pulses of light, the resulting half wave signal is memorized and memorized data is embedded in the nanosensor by continuing pulses of light, thereby forming long term memory. A desired loss of memory is enabled by reversing the reference potential, using a counter electrode washed with saline or extracellular fluid, using blocking conductive material, such as wool or cotton, or washing the nanosensor with extracellular fluid through the conductor.

Memory is enabled in the nanosensor by photonic reassembly of carbon, oxygen, fluoride (such as carbon tetra fluoride), and nitrogen bonds in amino acids, peptides and proteins embedded in cationic and anionic sites in the protein rhodopsin nanosensor of the fiber optic nanosensor operatively coupled with the laser diode. Charge sites in the photosensitive material, such as rhodopsin are identified and sites are memorized by repeated and/or continuous pulses of photonic light from the near infrared laser. The memory of charge is embedded in the photosensitive material of the nanosensor, and the nanosensor links to the brain neurotransmitters, such as dopamine, serotonin, aspartate, and glutamate.

The disclosed embodiments relate to live imaging of neuromolecules directly related to brain, body, and blood disorders, preferentially in mammalian patients and animals, through the periosteum covering the scalp above the skull that surrounds the brain's cranium. These embodiments are noninvasive, as molecules are imaged live without opening the skull. The embodiments use a series of polymeric protein nanosensors that exhibit photosensitive and electroactive properties. A photosensitive and electroactive protein, such as rhodopsin, is used with and without its chromophore, retinal, and includes a photovoltaic semiconductor, which is a rhodopsin complex catechol protein, referred to herein as rhodonine, which is derived from opsin as is rhodopsin.

Photons of light, in the near infrared spectral band, pass through fiber optic polymaterials of glass or plastic in the form of photonic bundles of quantum light energy. These fiber optic cables contain quanta photons of energy, and are electrically connected to a series of laser diodes, which are powered by a low wattage designed to reach approximately 30 mm into the neuroanatomy of the brain, such as the hippocampus and cortex of, for example, an epilepsy patient, which may be intractable to conventional drug treatments. Rhodopsin is in the core of the fiber optic material connected to the laser diodes.

Neurons are dynamically polarized cells that are responsible for electrochemically transmitting information throughout the nervous system. Scientists have characterized hundreds of neuron types based on location, morphology, and gene expression. In general, there are three main types of neurons: motor neurons, sensory neurons, and interneurons. Despite great variability in size and shape, most neurons share common morphological features including a cell body, dendrites, axon, and axon terminals.

In one embodiment, near infrared energy activates photoreceptors in the rhodopsin retinal nanosensor, which is in the core of the fiber optic of the laser module. When excited by light, polar covalent hydrogen bonds of carboxylic acid and amine moieties in rhodopsin retinal react to produce either positive or negative neuron proteins, thereby forming memory in the nanosensor and the target, for example, the neuron, enabling the photoelectromechanics, such as a memory chip that mimics the function of memory in animals and humans.

Molecules correlate with frequency, which is the number of cycles of photonic energy absorbed during a given period of time. In rhodonine complexes of rhodopsin, chemical bond transformations occur in a donor acceptor region of the semiconductor, rhodonine. In both examples, light induced chemical bond transformation creates, rearranges, polymerizes, catalyzes, and cleaves covalent hydrogen chemical bonds to manipulate molecular signals to one or more protonated or deprotonated hydrogen bond memory sites.

Memory sites in the neuron formed by near infrared include protonated electrons in the rhodopsin retinal nanosensor, such as in metarhodopsin 1 formed from rhodopsin and converted to metarhodopsin II, creating embedded cationic sites, whereas, in halorhodopsin, in its chemical transformation to lumirhodopsin, anionic memory sites are formed and memorized by a quantum of photon packets induced by light. The nanosensor provides memory by bleaching or changing color.

In a preferred embodiment, the photosensitive material in the nanosensor is a fluorescent protein, which is preferably rhodopsin. Rhodopsin is a protein polymer that absorbs blue green light and appears reddish purple during chemical transformation of memory sites embedded in the protein matrix of the nanosensor. Photosensitive electroactive polymers with blue light emitting laser/rhodopsin/rhodonine photodiodes using one or more photon lasers in the near infrared spectrum are described herein, but are not limited to the specific examples described herein. Rhodopsin is bonded covalently to lysine amino acid of 11 cis-retinal, preferably over a trans-isomer of retinal in the rhodopsin retinal complex.

Phototransduction of the memory function through light induced chemical bond transformation signals specific spectral and electrochemical waveforms at specific wavelengths and half wave potentials by anion/cation exchange. The generation of potentials is visualized by color changes in the fluorescent protein. Waveforms and redox waveforms are seen on a spectrometer and a potentiostat on-line via, for example a personal computer or cell phone.

Thus, the nanosensor remembers by performing the function of memorizing the signaling process through autotrain with continuing flashes of light. Although each autotrain may include a small amount of photonic energy, that is, high voltage energy at a number of volts through the photovoltaic effect, the final memory process in terms of quantum packets of energy is substantially more effective than each flash of light.

Photovoltaics are important components of semiconductors, and involve the production of volts from packets of photonic light energy. Photovoltaics also involve the generation of a potential difference at the terminals of an unbiased semiconductor diode, which includes a p positive-n negative heterojunction as a result of illumination with light having energy higher than the energy gap (Eg) of the semiconductor. At the n junction of the semiconductor is the electron, proton sink, or quantum hole, in which the memory site is protonated after having received excess protons from the p junction.

What this means for the nanosensor is that the part that rhodinone catechol protein plays in the nanosensor represents another advancement over conventional techniques as it relates to ESPT, which is the basis of optical voltaic memory in the disclosed embodiments. The advances provided by ESPT are faster by a factor of 1 over the factor of atomic observation for electron transfer without light ranging in the approximate range of $10^{-4}$ to $10^{-8}$ of a joule in the anode cathode semiconductor in contrast with non ESPT-based conventional techniques. Accordingly, the disclosed embodiments enable critical improvement over previous electrochemical and spectrophotometric devices, which include live imaging without opening the skull; and the use of ESPT.

The nanosensor signals from the brain are remembered by phototransduction of light photons, conversion to photovoltaic energy, which is further converted to photoelectrochemical imaging, and visualized by collecting photonic waveforms by a spectrometer, and collecting electronic waveforms by a potentiostat. Final waveform signaling live visualization occurs by DC-to-AC conversion on a computing device. A key to memory is absorption to adsorption to nanosensor through holes of the rhodopsin, and photons to volts to anions and cations in the nanosensor to cations and anions in the target.

FIG. 1 shows a nanosensor 10, in which electrons 12 flow from target molecules 14, such as dopamine, neorephrine, and serotonin that are being measured, to a graphite paste 16 disposed in the nanosensor 10. This electron movement causes a flow of charge that yields a current, which can be read on a strip chart recorder and/or computing device.

FIG. 2 shows an embodiment of the nanosensor 18 in accordance with one or more embodiments disclosed herein, which includes a photosensitive material, preferably a fluorescent protein, preferably rhodopsin, opsin 22, and/or combinations thereof disposed in a polymer shell 20. The nanosensor 18 is hydrogen bonded with the memory polymer shell 20 that includes lipids and/or oils. The nanosensor 18, in one embodiment, is mixed with other polymers with and/or without nucleic acids and/or aptamers, and the like, and/or combinations thereof. In another embodiment, the nanosensor 18 acts as a coat or external layer. In another embodiment, the nanosensor 18 is soaked in one or more of the above embodiments and/or combinations of embodiments.

The memory polymer shell 20 transduces a memory of the shape of a target molecule, which subsequently provides a peak signature for each target molecule. The memory of the target molecule is embedded within the spaces of the conductor or semiconductor device disposed in the nanosensor 18, which is organic and/or inorganic. A template of the target molecule is used to represent analytes for the diagnosis and treatment of brain, body, and blood diseases, as well as for studying the natural human condition. The shape of the target molecule includes pores that can be used as templates to represent other neuromolecules that appear in the form of a recognizable peak.

In another embodiment, memory transduction by the conducting or semiconducting device of the nanosensor 18 can be used to make templates of nanomaterials during, for example, the manufacture of bandages, adhesives, antiseptic closures for wound healing, and patches for drug delivery, such as that used in conjunction with diabetic patients and patients with melanoma. In addition, peptide-protein hydrogen bonding in the nanosensor 18 may include deoxyribose nucleic acid (DNA) that further bonds to form material templates, which can be used in designing surgeries concerning the brain, body, and blood, in vivo, in vitro, and/or in situ, for use in biochips, tissue chips, and brain repair.

Figure 3:
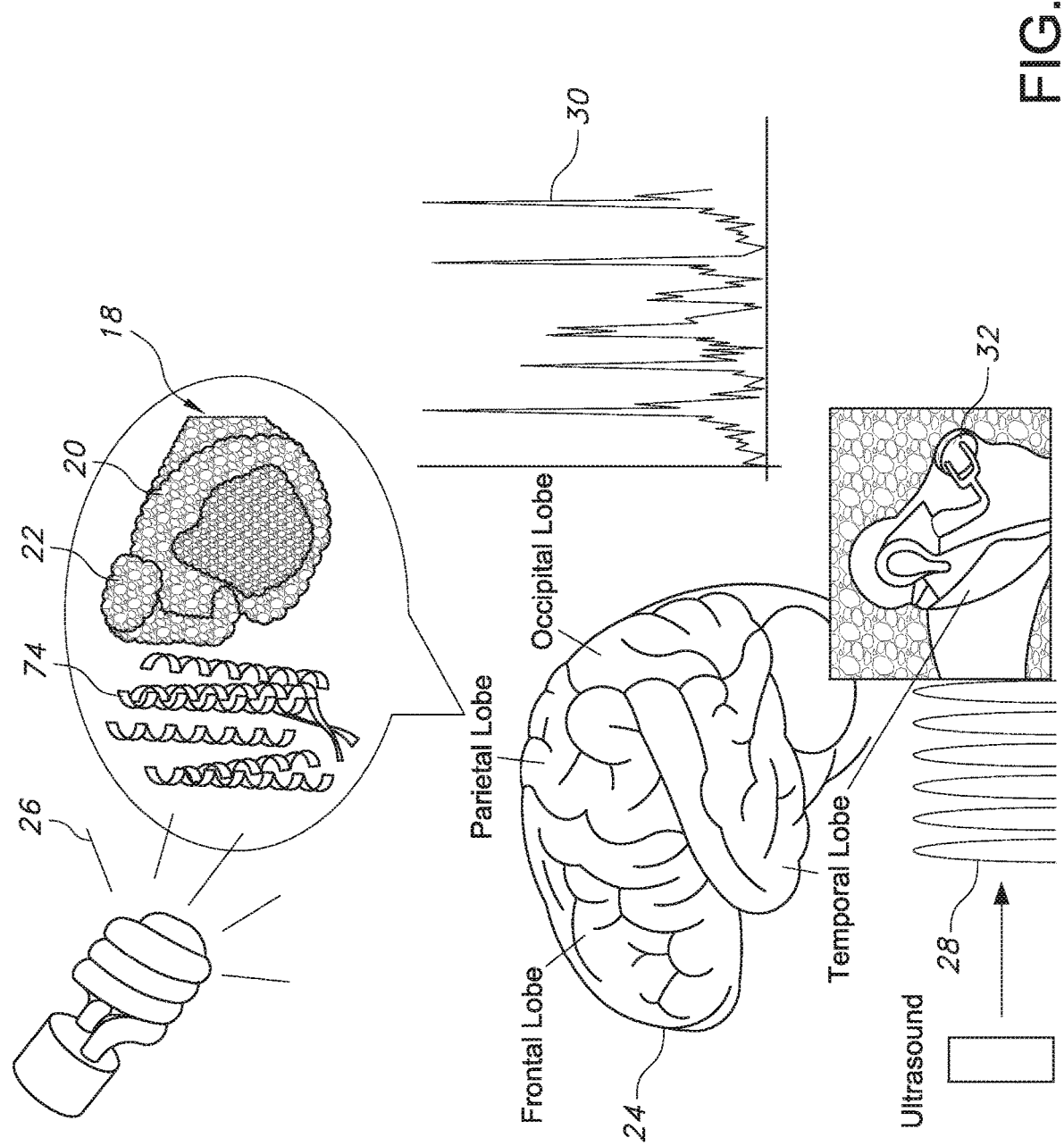
FIG. 3 shows the operation of the nanosensor in accordance with one or more of the disclosed embodiments.

FIG. 3 shows an embodiment of the nanosensor 18 for noninvasive and minimally invasive use in the brain, body, and/or blood, in vivo, in vitro, and/or in situ. Entry to the brain 24 is performed by converting photonic energy 26, such as near infrared energy, to electrochemical energy in order to track neurotransmitters without opening the skull. Ultraviolet or near-infrared photonic energy 26 is used by the nanosensor 18, with or without the polymer shell 20, to pass the blood-brain barrier. The photonic energy 26 is converted to electrochemical energy by retinol, retinoic acid, and retinal in the brain, blood, and body, particularly including, but not limited to, the eyes and skin. Ultrasound 28 bounces sound waves off, for example, the temporal bone and piezoelectric material (organic and/or inorganic) converts that sound to electrical units, such as volts. The tympanic membrane 32, which is not a bone, yet acoustically feasible for converting sound to volts, is used.

Electroactive signal patterns 30 of healthy, diseased, and treated states in humans and animals are provided, which can be observed using, for example, a mobile computing device in personalized medicine and point-of-care applications. It is to be noted that a fiber optic core laser unit, which provides the photonic energy 26, and the nanosensor 18 are smaller than a human hair.

Accordingly, the disclosed embodiments relate to a protein sensing nanosensor that includes a photosensitive material, such as rhodopsin and other molecules, such as retinal, opsin, rea channel rhodopsin, red shifted channel rhodopsin, and the like. The nanosensor is disposed in the core of a fiber optic cable 42, which is operatively coupled to, for example, a miniaturized near-infrared laser diode photodiode circuit 40 as is, for example, shown in the block diagram of FIG. 4. The fiber optic cable 42 as is, for example, shown in FIG. 5, includes the miniature rhodopsin nanosensor 18 shown in FIG. 2 embedded therein.

Figure 4:
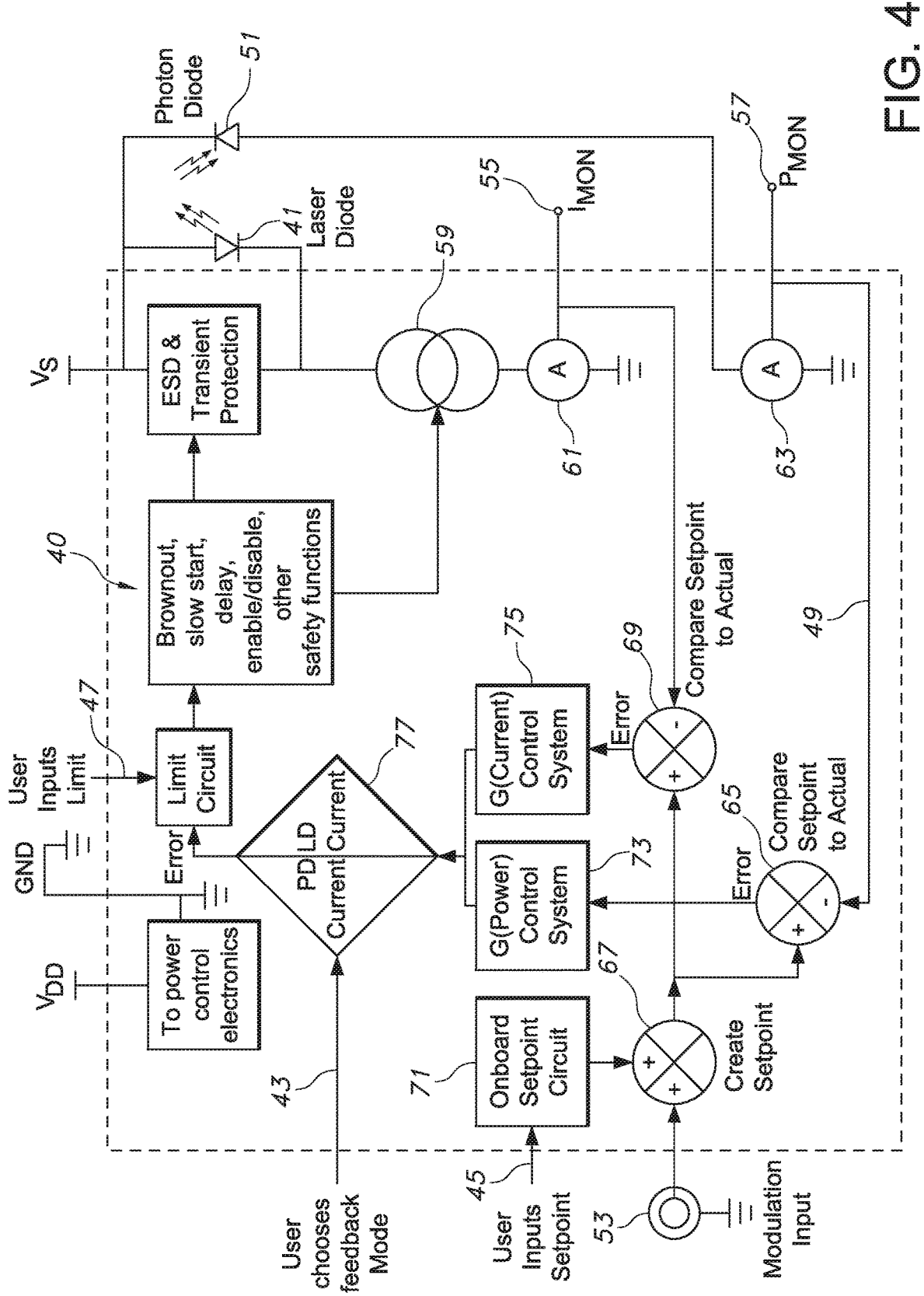
FIG. 4 is a block diagram of a miniaturized near infrared laser diode and photodiode circuit for use in accordance with one or more of the disclosed embodiments.
Figure 5:
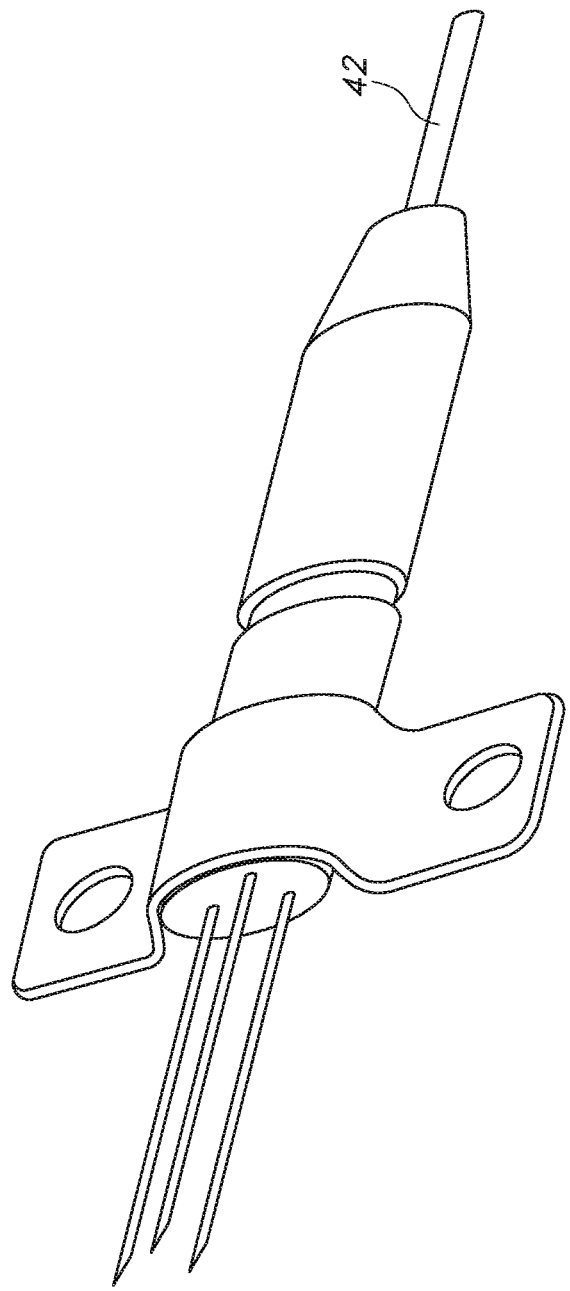

The block diagram shown in FIG. 4 is a laser diode driver circuit 40. The circuit 40 essentially controls current applied to a laser diode 41 based on a feedback mode 43, setpoint 45, modulation input 53, and input limit 47 selected by the user, as well as a feedback signal 49 derived from a photodiode 51. An analog signal, such as a sine wave, triangle wave scan, or square wave, is input to the laser diode driver circuit 40 at the modulation input 53. This analog signal is related to the actual current or power output by a transfer function. The function of the laser diode driver circuit 40 is to provide current to the laser diode 41. The wavy arrows near the laser diode 41 indicate light exiting the laser diode 41. The current applied to the laser diode 41 is monitored at node 55, and the power obtained from the photodiode 51 is monitored at node 57. The photodiode 51 produces a current substantially proportional to the output laser diode 41 optical power. The wavy arrows near the photodiode 51 indicate light entering the photodiode 51. A current source 59 provides current to the laser diode 41. An ammeter 61 provides a voltage Imon at node 55, which is representative of the current through the laser diode 41. An ammeter 63 provides a voltage Pmon at node 57, which is representative of the current through the photodiode 51.

The circuit 40 can operate in a current feedback mode or a power feedback mode using summing amplifiers 65, 69, mixer 67, setpoint circuit 71, power control system 73, current control system 75, and feedback mode selection circuit 77. Since setpoint, as determined by the setpoint circuit 71, is application specific, it must be adjustable by the user, which is typically provided by an adjustment mechanism, such as a trimpot. The power control system 73 determines how the error between setpoint and actual photodiode current is modified to make an electronic signal that appropriately drives the adjustable current source 59 to keep error to a minimum, which is used during the constant power mode operation. The current control system 75 determines how the error between setpoint and actual laser diode current is modified to make an electronic signal that appropriately drives the adjustable current source 59 to keep error to a minimum during the constant current mode operation.

The summing amplifiers 65, 69 are used to measure the difference between the setpoint and actual current, or to sum the onboard setpoint trimpot with an external analog modulation signal. The laser diode driver circuit enables control based on either laser diode current or photodiode current. If laser diode current is used as feedback, the control system keeps it constant by maintaining the output of the adjustable current source 59 constant in a constant current mode. If photodiode current is used as feedback, the control system maintains the photodiode current, and thus the laser diode optical power constant by varying the output of the adjustable current source to keep the optical power level constant in a constant power mode.

VDD is the symbol used to refer to the external power supply that feeds the control electronics of the circuit 40, which is typically 3.3 to 5 V DC. VS is the symbol used to refer to the external power supply that feeds the adjustable current source electronics, which is typically a DC voltage.

One key section of the laser diode driver circuit is the adjustable current source 59, which is also referred to as an output stage. The current source 59 responds to the control systems 73, 75 by driving current to the laser diode 41, which is between the supply voltage and current source 59.

The user inputs include the limit setpoint 45 (in terms of maximum laser diode current allowed to the laser diode), the operating setpoint, and whether the control variable is laser diode current or photodiode current. Additionally, if a remote setpoint is required, an analog modulation input is available.

The setpoint 45 is an analog voltage into the system, which can be created by a combination of onboard adjustment and the modulation input 53. In some cases, the modulation input 53 sums with the onboard setting. In other cases, the modulation input 53 subtracts from the onboard setting.

In order to determine how the system is functioning, the actual current level is compared to the setpoint current level. These two voltages are subtracted and the result is referred to as the error. In the case of the laser diode driver circuit 40, the actual current level can come from either the laser diode 41 or the photodiode 51. If laser diode current is used as feedback, the control system uses the error signal from the laser diode current, and the output of the adjustable current source 59 will not vary in the constant current mode. If photodiode current is used as feedback, the control system maintains the photodiode current, and thus the laser diode optical power constant by varying the output of the adjustable current source 59 in the constant power mode. The control system 73, 75 converts the error signal into a control signal for the laser diode current source 40, which is different in the constant power mode and constant current mode.

Figure 6:
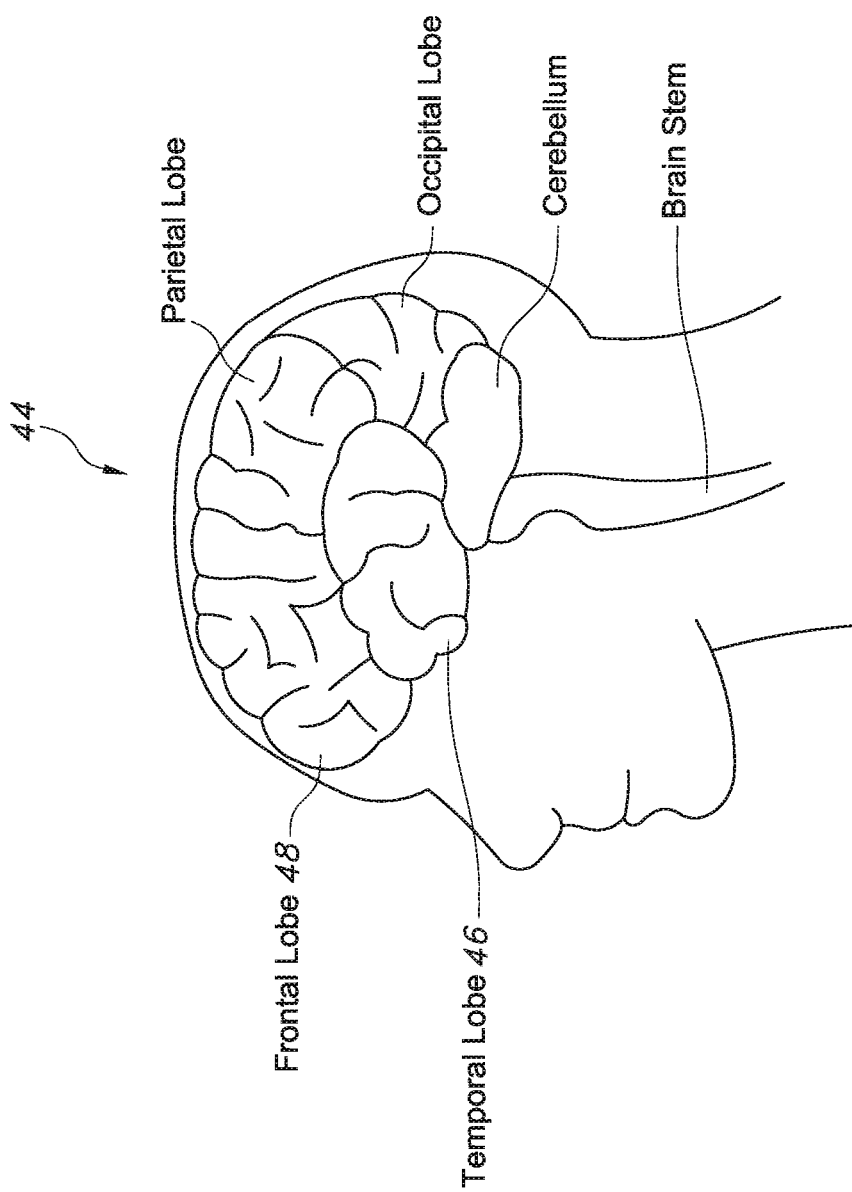
FIG. 6 shows a patient's brain.

Photons of near-infrared light rays are directed to the skull of the patient. The nanosensor 18 is inserted in the core of the fiber optic cable 42, and can be used with or without the organic or inorganic polymer. The fiber optic cable 42 is applied behind the ear of, for example, an epilepsy patient, and photons are directed toward the skull of the patient shown in FIG. 6 at the temporal lobe 46, such as the hippocampus. Another laser is disposed in contact with the skull 44 of the patient, such as at the frontal lobe 48 of the patient, and another laser is disposed at the scalp or periosteum above the skull of the patient.

Polystyrene is disposed in the core of the fiber optic cable 42, with refractive indices of 1.49 and 1.59, respectively. Generally, cladding of the fiber optic cable includes a silicone resin with a refractive index of approximately 1.46. A high refractive index difference is maintained between the core and the cladding. The photosensitive nanosensor 18, which is smaller than a human hair, is inserted in the core of the fiber optic cable, which is also smaller than a human hair.

The fiber optic cable 42 carries light pulses that bounce back on each other to produce photons of light.

Figure 7A:
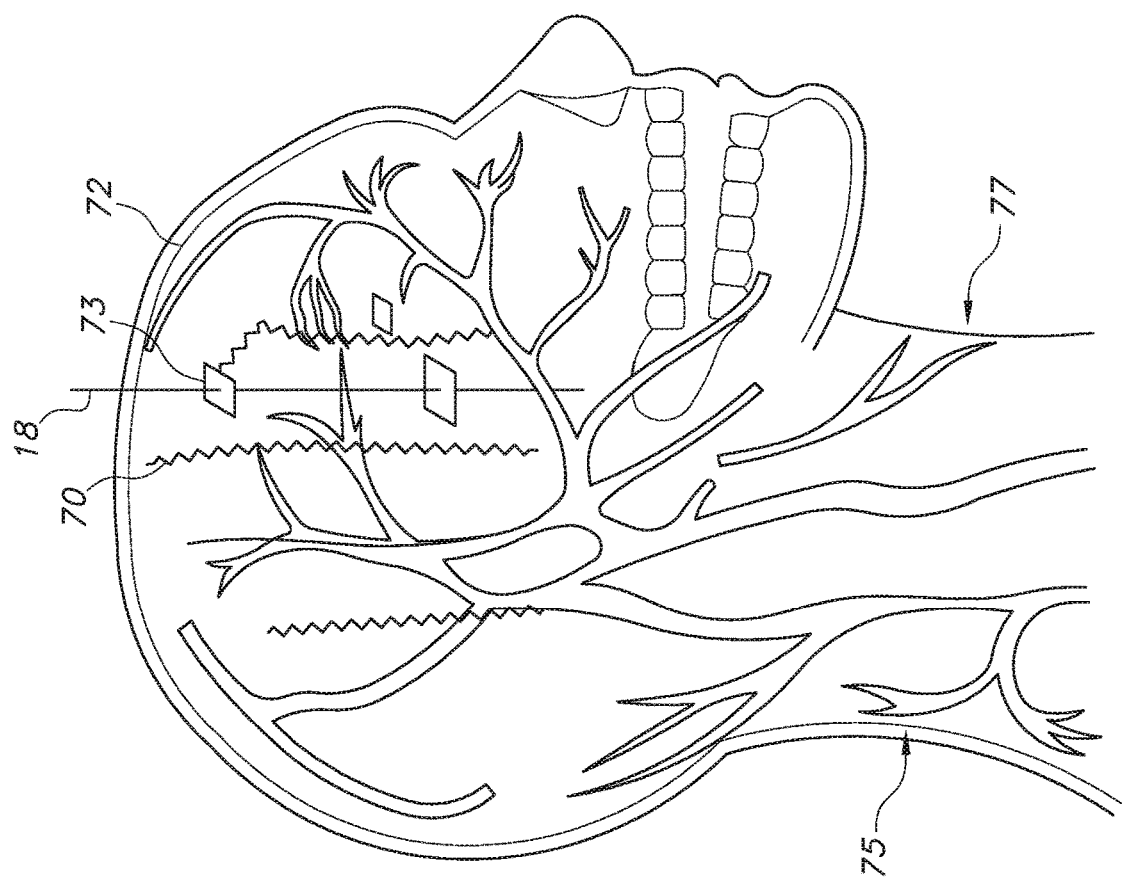
FIG. 7A shows a side view of the patient's skull and operation of the nanosensor in accordance with one or more of the disclosed embodiments.

FIG. 7A shows an application of the nanosensor 18. The circuit 40 is coupled to the nanosensor 18, which is placed in contact with the patient's skull 72. The fiber optic cable 42 in the nanosensor 18 acts as a waveguide for the near infrared laser in directing optical energy in the form of a rhodopsin photocurrent to and through the patient's skull 72, cortex 73, and brain. The rhodopsin photocurrent is directed through ligand ion gated channels 70, which also act as waveguides, through the patient's skull 72, cortex 73, and brain. A potentiostat 75 disposed inside the scapula of the patient's neck obtains an output of the photon driven electrochemical signals. An external spectrometer 77 is used to detect and represent light energy derived from the nanosensor 18 as the light energy passes through the patient's skull 72, cortex 73, and/or brain. The potentiostat 75 and spectrometer 77 are disposed in a miniaturized enclosure behind the patient's ear. Photonic light from the laser is converted to electrical energy by the photoelectric effect, and the generation of electrical potential to packets of photon energy is implemented by the fiber optic and rhodopsin nanosensor, which enables the photovoltaic effect in an np semiconductor.

The potentiostat 75 is used to control a three electrode cell during electroanalytical experiments. The potentiostat 75 functions by maintaining the electrical potential of a working electrode at a constant level with respect to a reference electrode by adjusting the current at an auxiliary electrode. The potentiostat 75 includes an electric circuit, which can be described in terms of operational amplifiers. Potentiostats are fundamental to modern electrochemical studies using three electrode systems for investigations of reaction mechanisms related to redox chemistry and other chemical phenomena. The dimensions of the resulting data depend on the experiment. In voltammetry, electric current in amps is plotted against electric potential in volts. The potentiostat 75 is configured to interface with a personal computer and operate through a dedicated software package. The automated software allows the user to rapidly shift between experiments and experimental conditions. The computer allows data to be stored and analyzed more effectively and accurately.

The spectrometer 77 measures properties of light over a specific portion of the electromagnetic spectrum, and is used in spectroscopic analysis to identify materials. The variable measured is most often the intensity of light, but can also, for example, be a polarization state. The independent variable is usually the wavelength of light or a unit directly proportional to the photon energy, such as reciprocal centimeters or electron volts, which has a reciprocal relationship to wavelength.

FIG. 7A shows the near infrared laser module with laser diode and photodiode fiber optic bundles and rhodopsin nanosensors disposed in the core of fiber optic cables. Laser diode fiber bundles 18, in which electrical energy in converted to light energy, photo diode fiber bundles, in which light energy is converted to electrical energy, and a spectrometer 77, in which the resulting spectral frequency is analyzed, are used in the laser module. The photonic/electrical change in potential produces a photovoltaic effect, which results in a semiconductor excited state proton transfer. High voltage photons provide an image of electrochemical half waveforms at specific volts and/or amps. Proteins, protonated and deprotonated hydrogen bonding signaling, and memorization using pulses of light from the laser module provides waveforms using the spectrometer 77 and potentiostat 75. Fluorescent proteins act as photoreceptors to receive light in the visible spectrum without requiring near infrared energy. Near infrared energy radiates 30 mm into the brain. Circuitry for implementation of the laser module is preferably disposed in one or more enclosures behind the ear of the patient within a predetermined distance from, for example, the hippocampus in, for example, epilepsy patients. ESPT at np heterojunctions of semiconductor memory sites is performed in proton deficit holes of spaces, which are referred to as electron proton holes at terminal amino acids, peptides of proteins, carboxylic acid groups, such as cationic meta rhodopsin 1 to 2, and aspartate and glutamate sites in halorhiodopsin producing anionic memory sites. Imaging electrochemical waveforms and spectral waveforms may be implemented in one or more devices. In the embodiment shown in FIG. 7B, the laser diodes and photodiode are selected for use separately and signaling is performed separately through the laser diodes and photodiodes using photonic bundles of fibers separately in the same module.

Rhodopsin is located in the cell membrane bilayer of neurons and produces optical signals in photons during its life cycle. The nanosensor 18 applies photonic energy through ion channels 70 that exist in the skull and brain, which includes arteries and veins as well. The ion channels 70 are shown in FIG. 7A.

The skull or cranium 72, which is approximately 8 mm in the human adult and smaller in infants, allows light to flow through the ligand gated ion channels 70 into neuroanatomic parts of the brain. The nanosensor 18 in conjunction with the circuit 40 enables photonic energy to reach neuro-anatomically desired neurons to treat various diseases. Rhodopsin, such as rea channel rhodopsin, channels light via photons and live streams rhodopsin through the ion channels 70 in the skull 72. Red shifted channel rhodopsin carries the optical signal intracranially to the hippocampus, which is a neuronal site used for the treatment of epilepsy, brain tumors, and memory dysfunction. Photonic energy is transduced to electrochemical signals using molecules, such as retinal rhodopsin.

The potentiostat 75 shown in FIG. 7A integrates the electroactive charge from photons to a photocurrent, thus converting electrical and/or electrochemical energy from various rea channel rhodopsins and other embodiments of the nanosensor 18. In voltammetry, information regarding an analyte is obtained by measuring the current as the potential is varied. A voltammetry alternating current (AC) controller provides the output signal from the brain to, for example, a laptop, data logger, or the like. Current-to-voltage converters convert alternating current (AC) to direct current (DC), preferably for use with circuits applicable to low-voltage electric circuits in voltammetry controllers. The photonic signal is imaged the spectrometer 77 in spectral form in color in wavelengths in terms of frequency, for example, and is correlated with electrochemical waveform signals in terms of current, voltage, and resistance.

Figure 7B:
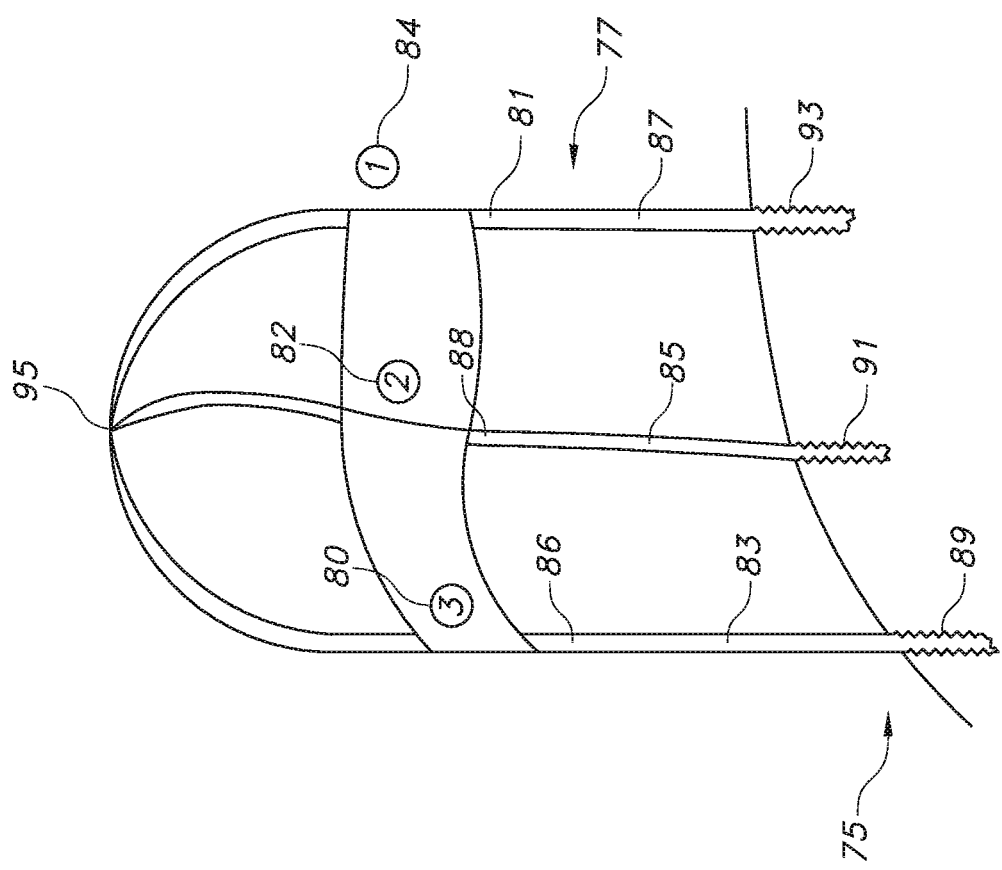
FIG. 7B shows an embodiment of an optical protein nanosensor system.

FIG. 7B shows an embodiment of an optical protein nanosensor system, in which three (3) laser diodes 80, 82, 84, which preferably emit optical energy having a 925 nm wavelength, are coupled to separate fiber optic cables 81, 86, 88, which are also coupled to three (3) photodiodes 83, 85, 87. Nanosensors 89, 91, 93 are coupled to each of the fiber optic bundles or cables 81, 86, 88. Each of the laser diodes 80, 82, 84 is coupled to the same or different connector(s) 95 to supply power to the laser diodes 80, 82, 84 during operation. The photodiodes are connected to the potentiostat 75 and to the spectrometer 77, which may be combined or separate. The nanosensor operates in essentially the same manner as the probe described in U.S. Pat. No. 5,938,903, that is, with reference, auxiliary, and working electrodes and the circuit shown in FIG. 15 of the '903 patent.

Figure 7C:
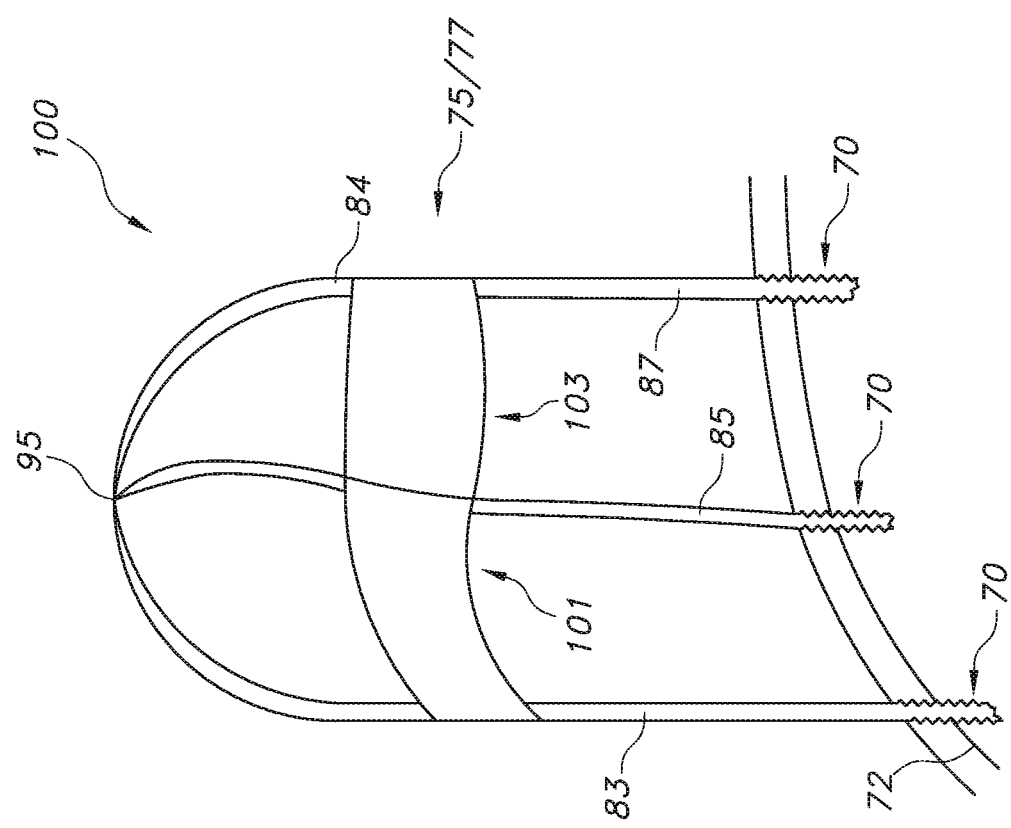
FIG. 7C shows another embodiment of the optical protein nanosensor system.

FIG. 7C shows another embodiment of the optical nanosensor system 100, in which the photodiodes 83, 85, 87 are utilized to collect photons and provide feedback to the laser diodes 80, 82, 84 via a feedback loop 101 to enable spectral and electrochemical waveform generation and analysis. The photonic energy is also fed to the spectrometer 77 as represented by arrow 103. The spectrometer and potentiostat are used to analyze the output of the module, in which both electrochemical and photochemical signals can be analyzed simultaneously.

Figure 7D:
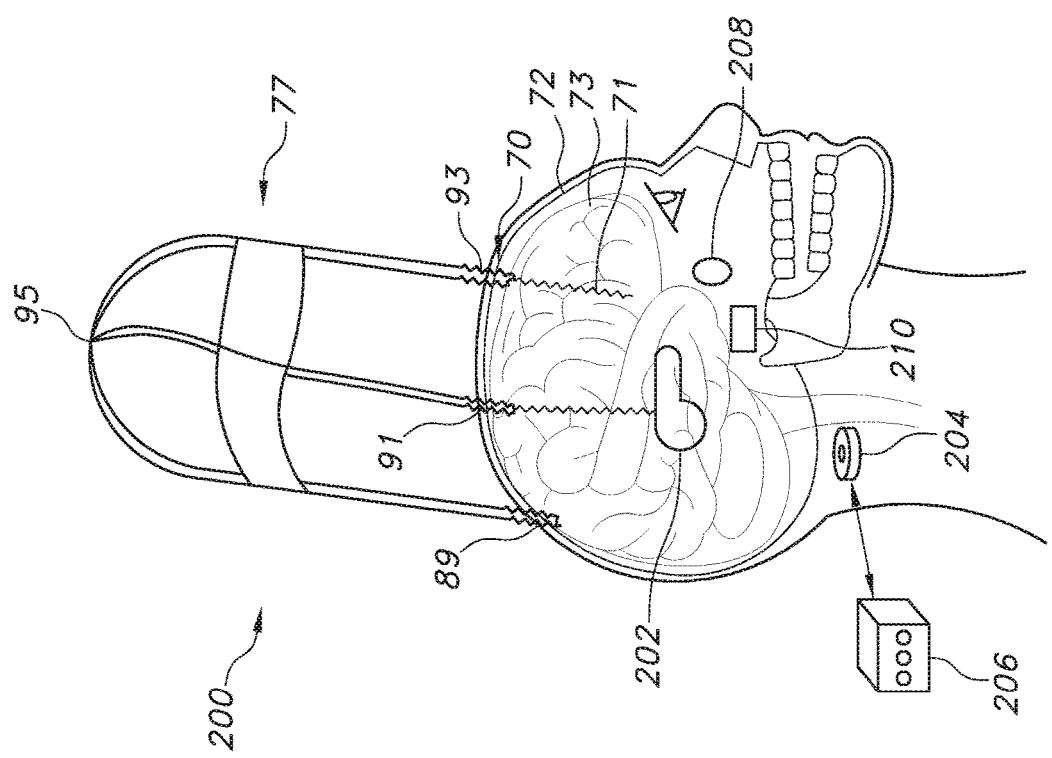
FIG. 7D shows another embodiment of the optical protein nanosensor system.

FIG. 7D shows another embodiment of the laser module unit 200 in conjunction with its application to the hippocampus 202 using waveguides 71 through the brain. In this embodiment 200, the potentiostat 75, piezoactuator 208, and commutator 204 are disposed in an enclosure behind the patient's ear 208.

Figure 8:
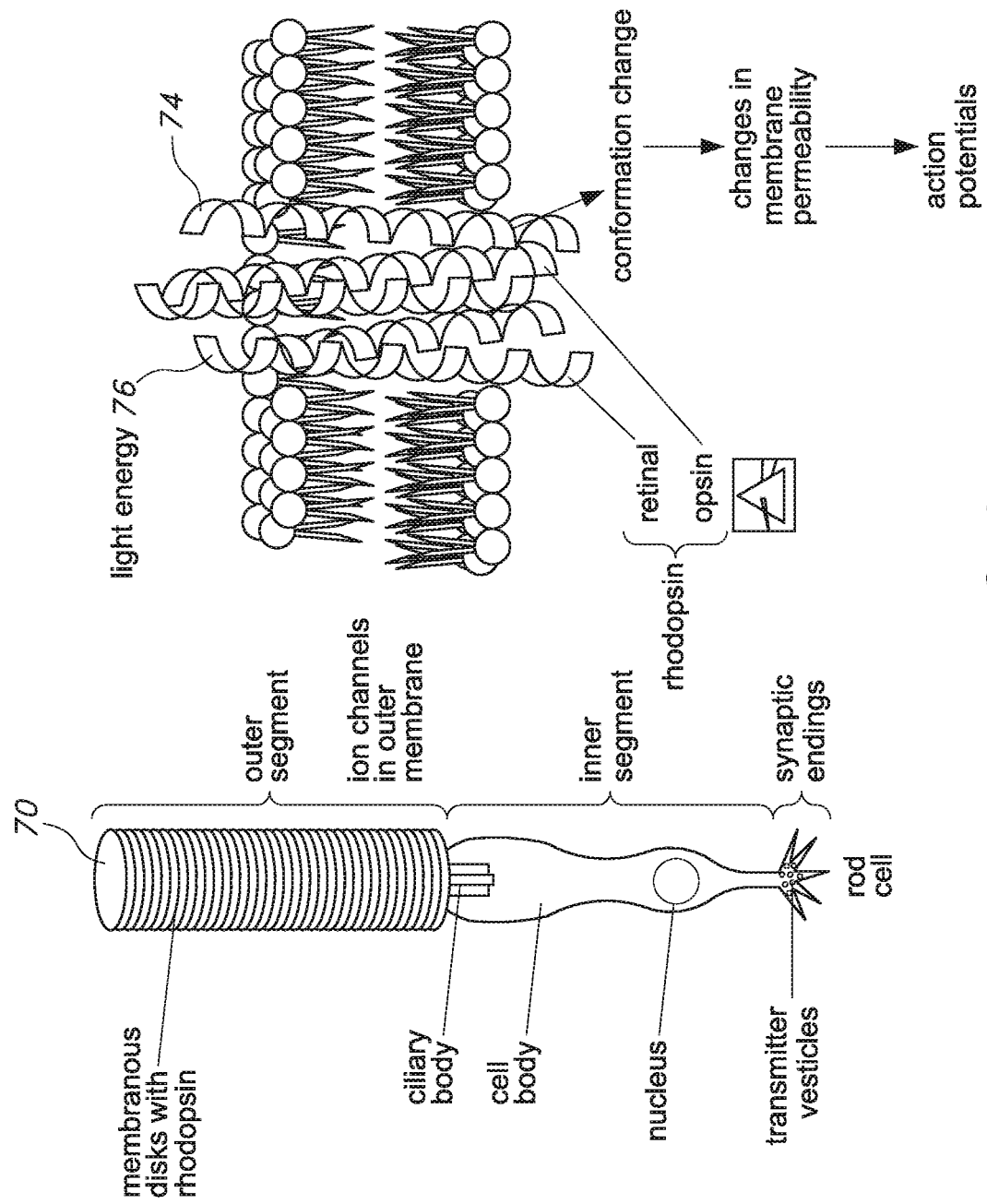
FIG. 8 shows mechanisms by which the nanosensor delivers optical energy to selected portions of a patient's brain.

Another embodiment includes the use of a metalloprotein photodiode that, with additional photodiodes and laser diodes, produce a threshold for ambient photonic energy to open ion channels in the skull. Thus, the protein, with or without the semiconductor photo and laser diode, use the channel rhodopsin-like nanosensor with or without organic and inorganic conductors with or without sources, such as algae, to open and close ion channels, such as hyperpolarizing ions, such as the amino acid, glycine. This feature is used to guide the signal through the brain. Sodium and/or potassium channel openers are not preferable since depolarization of neuronal circuits is not preferable in this embodiment. The signal from the nanosensor 18 travels through the cerebrospinal fluid surrounding the ion channels in the skull. Barriers to the signal include endothelial cells lining the capillary walls of glial cells, which are referred to as astrocytes, are overcome and not compromised. Movement of the light energy 76 as it travels through the skull and underlying membranes via, for example, rea channel rhodopsin 74 is shown in FIG. 8.

Figure 9:
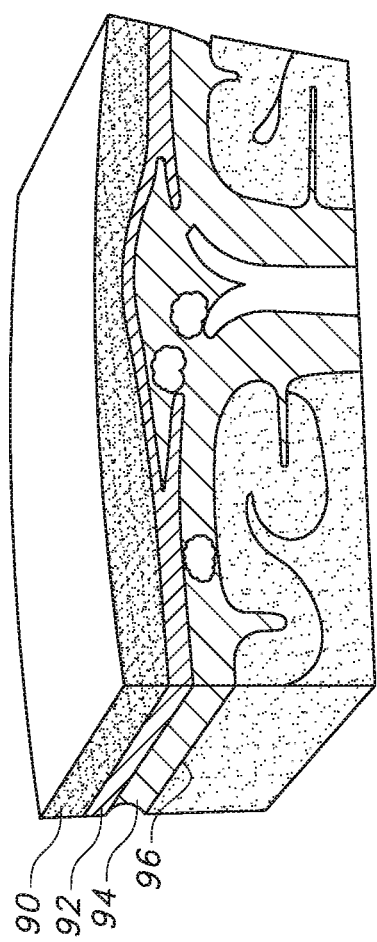
FIG. 9 shows a cross-section of a portion of the patient's skull and brain.

As shown in FIG. 9, the skull 90, which is illustrated as a flat surface, surrounds the head, and each lobe of the brain and face. FIG. 9 shows channels that are open for the passage of signals using the protein nanosensor 18 via photo and laser diodes and fiber optics through dura mater 92, arachnoid space 94, and pia mater 96. These channels connect with channels in the intracellular spaces and neurons of the brain. In the conventional art, the skull of an epilepsy patient is removed and placed in a −80 degree freezer while corticography and electroencephalograms are performed on the patient's brain. When the skull is replaced, arteries, veins, and channels in and among the skull, neurons, and glia connect autonomously. However, the disclosed embodiments advantageously render this procedure unnecessary.

Figure 10:
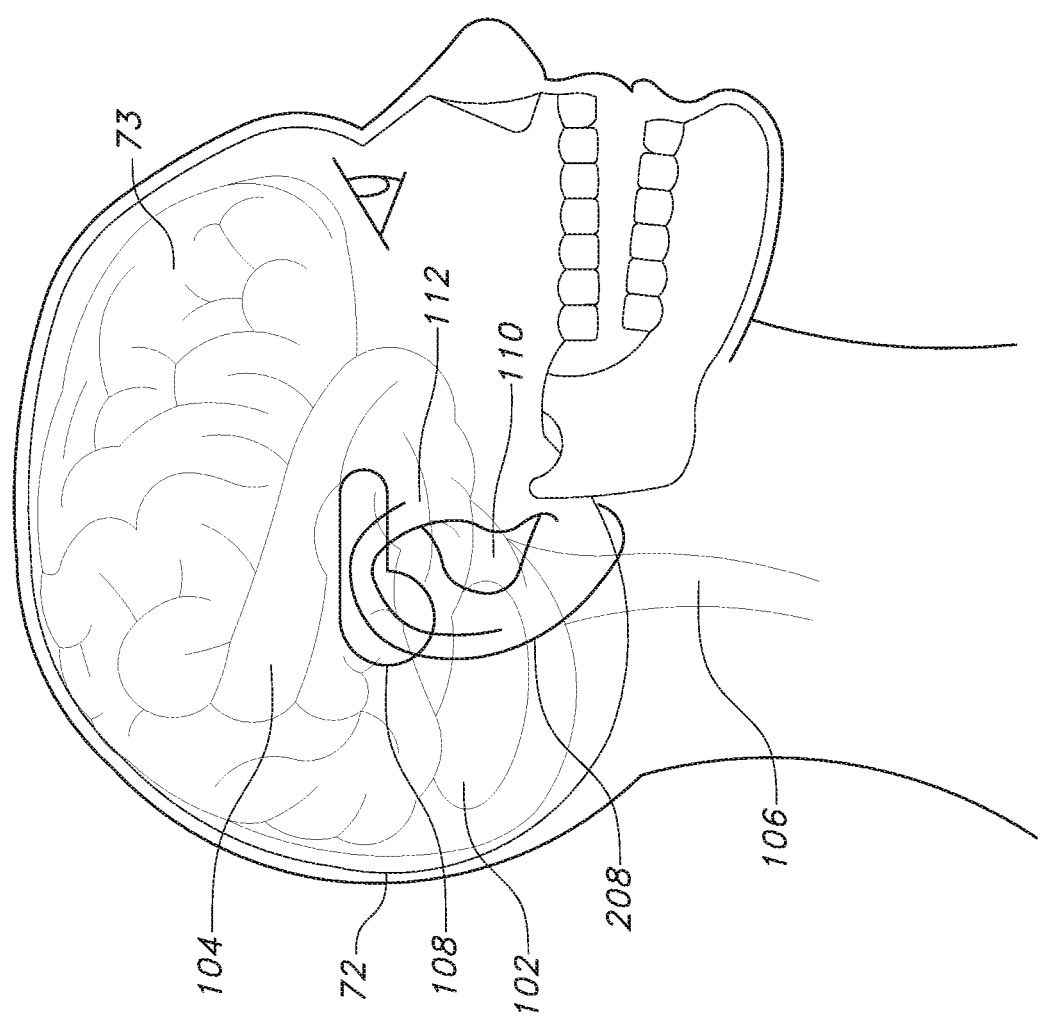
FIG. 10 shows locations of key parts of the brain that can be used to target diseases.

The embodiments disclosed herein are directly applicable to specific neurodegenerative and psychiatric disorders in humans and animals including, but not limited to, diseases of the motor and sensory systems in the brain, body, and blood. These interact with organ systems, such as the eye, brain, and skin in vivo, in vitro, and in situ. FIG. 10 shows the location of key parts of the brain that can be used to target some of these diseases, which are amenable to diagnosis and treatment strategies using the nanosensor.

The pons 100 serves as a message center between several areas in the brain from the cortex 72 to the cerebellum 102, and essentially from the dorsal or top of the brain to the ventral or bottom of the brain. Without the pons 100, there would be no communication, no passage of messages from neuron to neuron, for example.

The corpus callosum 104 serves as a message center passing information from one hemisphere to the other, from the left hemisphere to the right hemisphere and vice versa. Without the corpus callosum 104, there would be no communication across the hemispheres. The corpus callosum 104 is called a bridge between the two hemispheres, which is also called the white body bridge. Many diseases show crossover within and among many structures and multiple neurotransmitters.

Diseases that are evident from the brainstem 106 include vascular disease, stroke, brainstem gliomas and/or ependymomas, brainstem encephalitis (Bickerstaff s encephalitis), central pontine myelinolysis, Arnold-Chiari malformations, and syringobulbia. There is an involvement in the brainstem 106 with multiple cranial nerves and multiple blood vessels.

Central pontine mylinoysis overlaps with diseases of the brain stem 106. Critically important to the pons 100, in the temporal lobe, is the auditory system and disorders of the sensory system such as sensory gating dysfunction, seen in, for example, schizophrenic patients, and cocaine-induced schizophrenia. Lesch Nyhan disease is amenable for study with the disclosed nanosensor. Lesch Nyhan disease is an orphan disease involved with the dopaminergic motor system, in which children exhibit excessive debilitating chewing behavior.

In the mesocorticolimbic system 108, diseases are associated with the basal ganglia and movement disorders, but also involve cognition and emotion. This dopaminergic pathway system, as it is classically called, involves serotonin, for example, which leads from the A9 substantia nigra to the caudate nucleus and is notably related to Parkinson's disease and A10 ventral tegmentum to the nucleus accumbens, which is notably related to obsessive compulsive disease and drug abuse, for example. Cortex and cognitive effects are present. Alzheimer's, autism and schizophrenia are only a few conditions amenable for study with this nanosensor. The hippocampus 110 is included in the term, mesocorticolimbic. The hippocampus 110 is the memory center and essential for study in epilepsy patients and affective disorders, such as depression and anxiety, for example. The great cerebral vein, great cerebral artery, middle cerebral artery, and carotid artery are essential targets to use for study with the nanosensor per se and with blood flowometry methods for vascular studies.

The thalamus 112 is the region of the brain that first receives and processes information from the sensory nerves, and takes that information and relays it to other regions of the brain. Thus, damage to the thalamus 112 can cause changes in sensory perception, especially the perception of pain. Thalamic pain syndrome, the disorder most strongly associated with thalamus damage, is characterized by constant pain down one side of the body several weeks after a stroke. Numbness and paralysis can ensue. Temperature control is the function of the thalamus 112. The thalamus 112 is highly involved in neurodegenerative diseases, which are amenable for study using the nanosensor, such as Parkinson's disease, Alzheimer's disease, stroke, and initiation of the epilepsy seizure, which may be related to the thalamus 112.

Agenesis of the corpus callosum (ACC) 104 is associated with diseases of the corpus callosum 104. Agenesis of the corpus callosum 104 is rare, and is a congenital disorder in which there is a complete or partial absence of the corpus callosum 104. The disease occurs when the corpus callosum 104 fails to develop normally during pregnancy. Hypogenesis (partial formation), dysgenesis (malformation) of the corpus callosum, and hypoplasia (underdevelopment) of the corpus callosum are examples of other disorders of the corpus callosum 104.

Neurodegenerative, diseases such as those previously mentioned are critically associated with the cortex 73. Cognition is key insofar as the cortex 73 is concerned. Post anesthetic effects are associated with cognitive delay or deficit. Vision neurons reside in the prefrontal cortex in the frontal lobe and macular degeneration is associated with the occipital lobe. One may safely say, nearly all brain diseases are associated with the cortex 73. In epilepsy, for example, neocortical temporal lobe epilepsy is associated with the cortex 73.

Balance and classic limb ataxia are cardinal signs of cerebellar disease. In addition, the cerebellum 102 can be the target certain adverse effects of medication. Interestingly, cerebellar disorders can be related to cognition, emotionand some spectra of autism that may be non-motor disease related. Further, gender differences can readily be studied with the photonic nanosensor, and gender differences are not unique to any particular brain structure.

Figure 11:
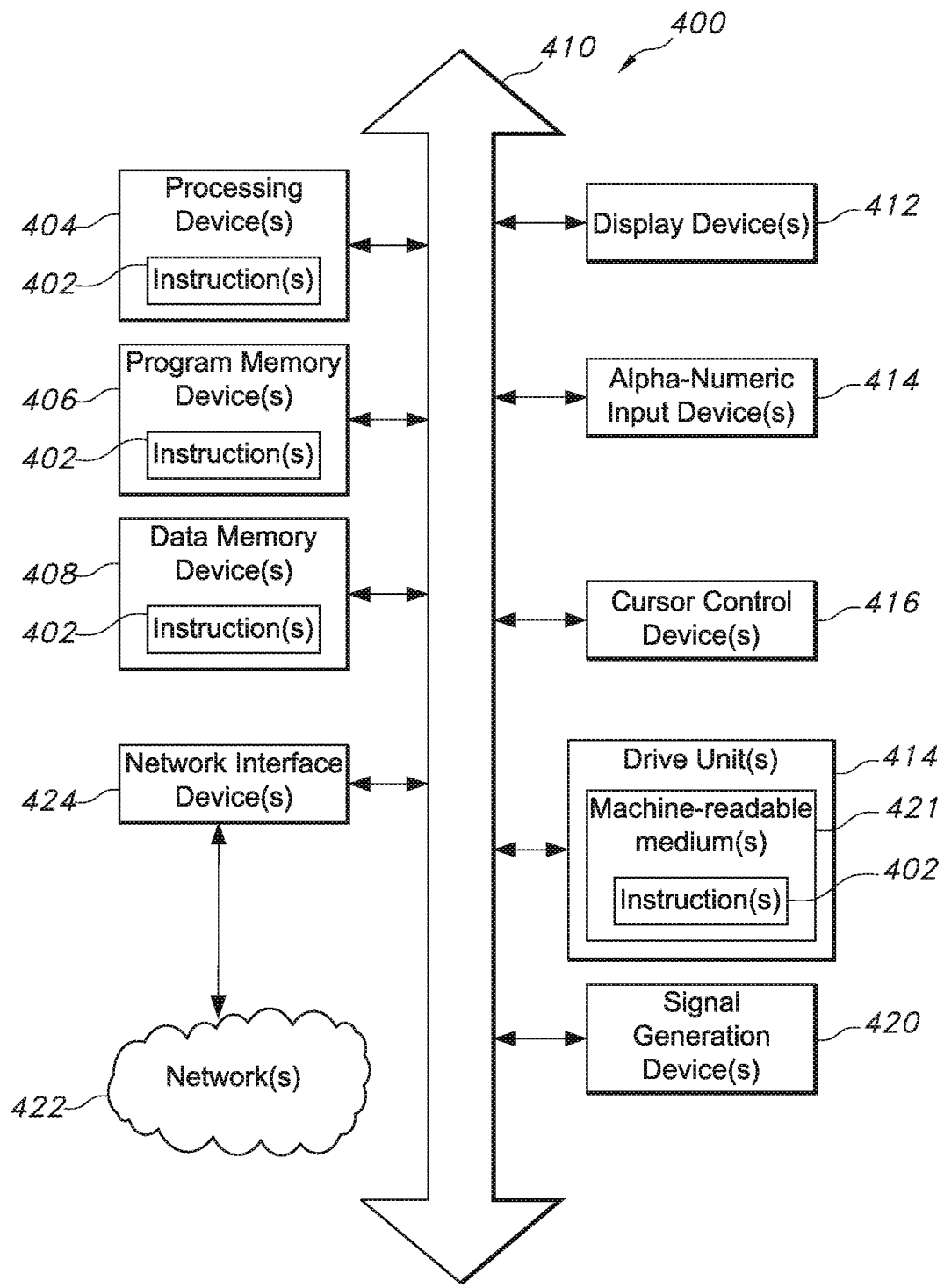
FIG. 11 is a block diagram of at least a portion of an exemplary machine in the form of a computing system that performs methods according to one or more embodiments disclosed herein.

One or more embodiments disclosed herein, or a portion thereof, may make use of software running on a computer or workstation. By way of example, only and without limitation, FIG. 11 is a block diagram of an embodiment of a machine in the form of a computing system 400, within which is a set of instructions 402 that, when executed, cause the machine to perform any one or more of the methodologies according to embodiments of the invention. In one or more embodiments, the machine operates as a standalone device; in one or more other embodiments, the machine is connected (e.g., via a network 422) to other machines. In a networked implementation, the machine operates in the capacity of a server or a client user machine in a server-client user network environment. Exemplary implementations of the machine as contemplated by embodiments of the invention include, but are not limited to, a server computer, client user computer, personal computer (PC), tablet PC, personal digital assistant (PDA), cellular telephone, mobile device, palmtop computer, laptop computer, desktop computer, communication device, personal trusted device, web appliance, network router, switch or bridge, or any machine capable of executing a set of instructions (sequential or otherwise) that specify actions to be taken by that machine.

The computing system 400 includes a processing device(s) 404 (e.g., a central processing unit (CPU), a graphics processing unit (GPU), or both), program memory device(s) 406, and data memory device(s) 408, which communicate with each other via a bus 410. The computing system 400 further includes display device(s) 412 (such as a liquid crystal display (LCD), flat panel, solid state display, or cathode ray tube (CRT)). The computing system 400 includes input device(s) 414 (e.g., a keyboard), cursor control device(s) 416 (e.g., a mouse), disk drive unit(s) 418, signal generation device(s) 420 (e.g., a speaker or remote control), and network interface device(s) 424, operatively coupled together, and/or with other functional blocks, via bus 410.

The disk drive unit(s) 418 includes machine-readable medium(s) 426, on which is stored one or more sets of instructions 402 (e.g., software) embodying any one or more of the methodologies or functions herein, including those methods illustrated herein. The instructions 402 may also reside, completely or at least partially, within the program memory device(s) 406, the data memory device(s) 408, and/or the processing device(s) 404 during execution thereof by the computing system 400. The program memory device(s) 406 and the processing device(s) 404 also constitute machine-readable media. Dedicated hardware implementations, such as but not limited to ASICs, programmable logic arrays, and other hardware devices can likewise be constructed to implement methods described herein. Applications that include the apparatus and systems of various embodiments broadly comprise a variety of electronic and computer systems. Some embodiments implement functions in two or more specific interconnected hardware modules or devices with related control and data signals communicated between and through the modules, or as portions of an ASIC. Thus, the example system is applicable to software, firmware, and/or hardware implementations.

The term "processing device" as used herein is intended to include any processor, such as, for example, one that includes a CPU (central processing unit) and/or other forms of processing circuitry. Further, the term "processing device" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the display device(s) 412, input device(s) 414, cursor control device(s) 416, signal generation device(s) 420, etc., can be collectively referred to as an "input/output interface," and is intended to include one or more mechanisms for inputting data to the processing device(s) 404, and one or more mechanisms for providing results associated with the processing device(s). Input/output or I/O devices (including but not limited to keyboards (e.g., alpha-numeric input device(s) 414, display device(s) 412, and the like) can be coupled to the system either directly (such as via bus 410) or through intervening input/output controllers (omitted for clarity).

In an integrated circuit implementation of one or more embodiments of the invention, multiple identical die are typically fabricated in a repeated pattern on a surface of a semiconductor wafer. Each such die may include a device described herein, and may include other structures and/or circuits. The individual dies are cut or diced from the wafer, then packaged as integrated circuits. One skilled in the art would know how to dice wafers and package die to produce integrated circuits. Any of the exemplary circuits or method illustrated in the accompanying figures, or portions thereof, may be part of an integrated circuit. Integrated circuits so manufactured are considered part of this invention.

An integrated circuit in accordance with the embodiments of the present invention can be employed in essentially any application and/or electronic system in which buffers are utilized. Suitable systems for implementing one or more embodiments of the invention include, but are not limited to, personal computers, interface devices (e.g., interface networks, high-speed memory interfaces (e.g., DDR3, DDR4), etc.), data storage systems (e.g., RAID system), data servers, etc. Systems incorporating such integrated circuits are considered part of embodiments of the invention. Given the teachings provided herein, one of ordinary skill in the art will be able to contemplate other implementations and applications.

In accordance with various embodiments, the methods, functions or logic described herein is implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement the methods, functions or logic described herein.

The embodiment contemplates a machine-readable medium or computer-readable medium containing instructions 402, or that which receives and executes instructions 402 from a propagated signal so that a device connected to a network environment 422 can send or receive voice, video or data, and to communicate over the network 422 using the instructions 402. The instructions 402 are further transmitted or received over the network 422 via the network interface device(s) 424. The machine-readable medium also contains a data structure for storing data useful in providing a functional relationship between the data and a machine or computer in an illustrative embodiment of the systems and methods herein.

While the machine-readable medium 402 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform anyone or more of the methodologies of the embodiment. The term "machine-readable medium" shall accordingly be taken to include, but not be limited to: solid-state memory (e.g., solid-state drive (SSD), flash memory, etc.); read-only memory (ROM), or other non-volatile memory; random access memory (RAM), or other re-writable (volatile) memory; magneto-optical or optical medium, such as a disk or tape; and/or a digital file attachment to e-mail or other self-contained information archive or set of archives is considered a distribution medium equivalent to a tangible storage medium. Accordingly, the embodiment is considered to include anyone or more of a tangible machine-readable medium or a tangible distribution medium, as listed herein and including art-recognized equivalents and successor media, in which the software implementations herein are stored.

It should also be noted that software, which implements the methods, functions and/or logic herein, are optionally stored on a tangible storage medium, such as: a magnetic medium, such as a disk or tape; a magneto-optical or optical medium, such as a disk; or a solid state medium, such as a memory automobile or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein and other equivalents and successor media, in which the software implementations herein are stored.

Although the specification describes components and functions implemented in the embodiments with reference to particular standards and protocols, the embodiment are not limited to such standards and protocols.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments are utilized and derived therefrom, such that structural and logical substitutions and changes are made without departing from the scope of this disclosure. Figures are also merely representational and are not drawn to scale. Certain proportions thereof are exaggerated, while others are decreased. Accordingly, the specification and drawings are to be regarded in an illustrative rather than a restrictive sense.

Such embodiments are referred to herein, individually and/or collectively, by the term "embodiment" merely for convenience and without intending to voluntarily limit the scope of this application to any single embodiment or inventive concept if more than one is in fact shown. Thus, although specific embodiments have been illustrated and described herein, it should be appreciated that any arrangement calculated to achieve the same purpose are substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single embodiment. Thus the following claims are hereby incorporated into the detailed description, with each claim standing on its own as a separate example embodiment.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single embodiment. Thus the following claims are hereby incorporated into the Detailed Description, with each claim standing on its own as separately claimed subject matter.

Although specific example embodiments have been described, it will be evident that various modifications and changes are made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and without limitation, specific embodiments in which the subject matter are practiced. The embodiments illustrated are described in sufficient detail to enable those skilled in the art to practice the teachings herein. Other embodiments are utilized and derived therefrom, such that structural and logical substitutions and changes are made without departing from the scope of this disclosure. This Detailed Description, therefore, is not to be taken in a limiting sense, and the scope of various embodiments is defined only by the appended claims, along with the full range of equivalents to which such claims are entitled.

Given the teachings provided herein, one of ordinary skill in the art will be able to contemplate other implementations and applications of the techniques of the disclosed embodiments. Although illustrative embodiments have been described herein with reference to the accompanying drawings, it is to be understood that these embodiments are not limited to the disclosed embodiments, and that various other changes and modifications are made therein by one skilled in the art without departing from the scope of the appended claims.

What is claimed is:

1. A nanosensor, comprising:
   an imaging component that uses photonic energy to generate a photocurrent that represents a molecular parameter, the imaging component comprising a photosensitive material and at least one of a laser diode and a photodiode; and
   a memory component that stores the representation of the molecular parameter, the memory component comprising at least one of a vitamin, a lipid, a carbon allotrope and carbon tetra fluoride;
   wherein the photosensitive material comprises a fluorescent protein, and wherein phototransduction of a memory function of the memory component is performed by light induced chemical bond transformation signaling specific spectral and electrochemical waveforms at specific wavelengths and half wave potentials through anion/cation exchange, whereby generation of the half wave potentials is visualized by color changes in the fluorescent protein.

2. The nanosensor, as defined by claim 1, wherein the photosensitive material further comprises at least one of a protein, a glycoprotein, a protease, a peptide, an amino acid, an opsin, a retinal, retinoic acid, retinol, rhodopsin, bathorhodopsin, lumirhodopsin, metarhodopsin 1, metarhodopsin 11, lumirhodopsin, trans-retinal, purple membrane proton pump protein microbe from a class of helobacteria, a eukaryote, a prokaryote and a vitamin.

3. The nanosensor, as defined by claim 1, wherein the memory component in the nanosensor transduces a memory profile of a half wave of a molecule, which provides a peak signature associated with the molecule in an excited state proton transfer (ESPT).

4. The nanosensor, as defined by claim 1, further comprising a potentiostat, wherein the potentiostat is configured to monitor photoelectrochemical current derived from the imaging component.

5. The nanosensor, as defined by claim 1, further comprising a spectrometer, wherein the spectrometer is configured to detect and represent light energy derived from the imaging component.

6. The nanosensor, as defined by claim 1, wherein the laser diode is configured to be disposed on a surface of skin proximate a brain and provides low wattage near infrared energy configured to extend approximately 30 mm into neuroanatomy of the brain relative to the surface of the skin.

7. The nanosensor, as defined by claim 1, wherein the imaging component further comprises at least one of a conductor and a semiconductor.

8. The nanosensor, as defined by claim 7, wherein the conductor comprises at least one of a silica-containing material and a piezoelectric material.

9. The nanosensor, as defined by claim 7, wherein the semiconductor comprises tetrafluoromethane.

10. The nanosensor, as defined by claim 1, wherein the imaging component further comprises rhodopsin, the memory component comprising carbon fullerene, the rhodopsin and carbon fullerene being disposed in a polymer shell.

11. The nanosensor, as defined by claim 1, further comprising a driver circuit configured for controlling a current applied to a laser diode of the imaging component as a function of at least one of a modulation input signal, a feedback signal, and one or more user-selectable input signals.

12. The nanosensor, as defined by claim 11, wherein the one or more user-selectable input signals comprise at least one of a feedback mode signal, a setpoint signal, and an input limit signal.

13. The nanosensor, as defined by claim 11, wherein the modulation input signal is related to an actual current or power output of the laser diode by a transfer function, the modulation input signal comprising at least one of a sine wave signal, a triangle wave signal and a square wave signal.

14. The nanosensor, as defined by claim 11, wherein the driver circuit comprises:
an adjustable current source operatively coupled with the laser diode for providing current to the laser diode; and
at least one of: (i) a power control circuit configured to determine an error between a prescribed setpoint selected by a user and a measured photodiode current, the photodiode current being indicative of output power of the laser diode, the power control circuit generating a first control signal for controlling the adjustable current source to keep error to a minimum during a constant power mode of operation of the driver circuit; and (ii) a current control circuit configured to determine an error between the prescribed setpoint and a measured laser diode current, the current control circuit generating a second control signal for controlling the adjustable current source to keep error to a minimum during a constant current mode of operation of the driver circuit.

15. The nanosensor, as defined by claim 1, further comprising a piezoelectric element, the piezoelectric element being configured to transduce movements of a patient in response to a photonic sound pulse stimulus into an electrical current that distinguishes firing from non-firing neurons.

16. A method of sensing polymers, comprising:
converting, using an imaging component, photonic energy into electrochemical energy to generate a photocurrent that represents a molecular parameter, the imaging component comprising a photosensitive material and at least one of a laser diode and a photodiode, the photosensitive material comprising a fluorescent protein;
storing, using a memory device, the representation of the molecular parameter, the memory device comprising at least one of a vitamin, a lipid, a carbon allotrope and carbon tetrafluoride; and
performing phototransduction of a memory function of the memory component by light induced chemical bond transformation signaling specific spectral and electrochemical waveforms at specific wavelengths and half wave potentials through anion/cation exchange, whereby generation of the half wave potentials is visualized by color changes in the fluorescent protein.

17. The method of sensing polymers as defined by claim 16, wherein the photosensitive material further comprises at least one of a protein, a glycoprotein, a protease, a peptide, an amino acid, an opsin, a retinal, retinoic acid, retinol, rhodopsin, bathorhodopsin, lumirhodopsin, metarhodopsin 1, metarhodopsin 11, lumirhodopsin, trans-retinal, purple membrane proton pump protein microbe from a class of helobacteria, a eukaryote, a prokaryote and a vitamin.

18. The method of sensing polymers, as defined by claim 16, further comprising:
transducing a memory profile of a half wave of a molecule; and
providing a peak signature associated with the molecule in an excited state proton transfer (ESPT).

19. The method of sensing polymers, as defined by claim 16, further comprising monitoring photoelectrochemical current derived from the imaging component using a potentiostat.

20. The method of sensing polymers, as defined by claim 16, further comprising detecting and representing light energy derived from the imaging component using a spectrometer.

21. The method of sensing polymers, as defined by claim 16, further comprising positioning the laser diode on a surface of skin proximate a brain, and configuring the laser diode to provide low wattage near infrared energy to extend approximately 30 mm into neuroanatomy of the brain relative to the surface of the skin.

22. The method of sensing polymers, as defined by claim 16, further comprising configuring the imaging component to comprise at least one of a conductor and a semiconductor.

23. The method of sensing polymers, as defined by claim 22, further comprising configuring the conductor to comprise at least one of a silica-containing material and a piezoelectric material.

24. The method of sensing polymers, as defined by claim 22, further comprising configuring the semiconductor to comprise tetrafluoromethane.

25. The method of sensing polymers, as defined by claim 16, further comprising:
configuring the imaging component to comprise rhodopsin;
configuring the memory device to comprise carbon fullerene; and
disposing the rhodopsin and carbon fullerene in a polymer shell.

* * * * *

UNITED STATES PATENT AND TRADEMARK OFFICE
CERTIFICATE OF CORRECTION

PATENT NO. : 11,197,615 B2
APPLICATION NO. : 16/074254
DATED : December 14, 2021
INVENTOR(S) : Broderick It is certified that error appears in the above-identified patent and that said Letters Patent is hereby corrected as shown below:

In the Claims

Column 26, Lines 37-42: now reads "at least one of a protein, a glycoprotein, a protease, a peptide, an amino acid, an opsin, a retinal, retinoic acid, retinol, rhodopsin, bathorhodopsin, lumirhodopsin, metarhodopsin 1, metarhodopsin 11, lumirhodopsin, trans-retinal, purple membrane proton pump"

should read --at least one of a protein, a glycoprotein, a protease, a peptide, an amino acid, an opsin, a retinal, retinoic acid, retinol, rhodopsin, bathorhodopsin, lumirhodopsin, metarhodopsin 1, metarhodopsin 11, trans-retinal, purple membrane proton pump--

Column 28, Lines 9-14: now reads "at least one of a protein, a glycoprotein, a protease, a peptide, an amino acid, an opsin, a retinal, retinoic acid, retinol, rhodopsin, bathorhodopsin, lumirhodopsin, metarhodopsin 1, metarhodopsin 11, lumirhodopsin, trans-retinal, purple membrane proton pump"

should read --at least one of a protein, a glycoprotein, a protease, a peptide, an amino acid, an opsin, a retinal, retinoic acid, retinol, rhodopsin, bathorhodopsin, lumirhodopsin, metarhodopsin 1, metarhodopsin 11, trans-retinal, purple membrane proton pump--

Signed and Sealed this
Twenty-second Day of November, 2022

Katherine Kelly Vidal
*Director of the United States Patent and Trademark Office*